(12) United States Patent
Kim et al.

(10) Patent No.: US 11,236,309 B2
(45) Date of Patent: Feb. 1, 2022

(54) RECOMBINANT VECTOR AND METHOD FOR PRODUCING RECONSTITUTED CYTOCHROME P450 OXYGENASE-REDUCTASE FUSION PROTEIN USING THE SAME

(71) Applicant: INDUSTRY FOUNDATION OF CHONNAM NATIONAL UNIVERSITY, Gwangju (KR)

(72) Inventors: Geun Joong Kim, Gwangju (KR); Chul Ho Yun, Sejong-si (KR); Dae Eun Cheong, Gwangju (KR); Su Kyoung Yoo, Gwangju (KR); Hye Ji Choi, Jeollanam-do (KR); Thien Kim Le, Gwangju (KR)

(73) Assignee: INDUSTRY FOUNDATION OF CHONNAM NATIONAL UNIVERSITY, Gwangju (KR)

( * ) Notice: Subject to any disclaimer, the term of this patent is extended or adjusted under 35 U.S.C. 154(b) by 0 days.

(21) Appl. No.: 16/995,168

(22) Filed: Aug. 17, 2020

(65) Prior Publication Data

US 2021/0355456 A1    Nov. 18, 2021

(30) Foreign Application Priority Data

May 13, 2020 (KR) .................. 10-2020-0057020

(51) Int. Cl.
| | |
|---|---|
| C12N 9/02 | (2006.01) |
| C12N 15/70 | (2006.01) |
| C07K 14/32 | (2006.01) |
| C12P 3/00 | (2006.01) |

(52) U.S. Cl.
CPC .................. C12N 9/0042 (2013.01)

(58) Field of Classification Search
None
See application file for complete search history.

(56) References Cited

U.S. PATENT DOCUMENTS

2011/0243849 A1    10/2011 Marletta et al.

FOREIGN PATENT DOCUMENTS

| KR | 10-2002-0034353 A | 5/2002 |
| KR | 10-2018-0023735 A | 3/2018 |
| KR | 10-2000490 B1 | 10/2019 |

OTHER PUBLICATIONS

Sarah Zernia et al., "Peptide-mediated specific immobilization of catalytically active cytochrome P450 BM3 variant", Bioconjugate Chem., 2016 DOI: 10.1021/acs.bioconjchem.6b00074.
Kristen S Swithers et al., "Conservation of intron and intein insertion sites: implications for life histories of parasitic genetic elements", BMC Evolutionary Biology, vol. 9:303, 2009.
Jacqueline Ellis et al., "Domain Motion in Cytochrome P450 Reductase Conformational Equilibria Revealed By NMR and Small-Angle X-Ray Scattering", The Journal of Biological Chemistry vol. 284, No. 52, pp. 36628-36637, Dec. 25, 2009.
Andrea L. M. Spencer et al., "Protein/Protein Interactions in the Mammalian Heme Degradation Pathway Heme Oxygenase-2, Cytochrome P450 Reductase, and Biliverdin Reductase", The Journal of Biological Chemistry vol. 289, No. 43, pp. 29836-29858, Oct. 24, 2014.
A. Sesilja Aranko et al., "Structure-based engineering and comparison of novel split inteins for protein ligation", Mol. BioSyst., vol. 10, pp. 1023-1034, 2014.
A.Sesilja Aranko et al., "Review; Nature's recipe for splitting inteins", Protein Engineering, Design & Selection vol. 27 No. 8 pp. 263-271, 2014, doi:10.1093/protein/gzu028.

*Primary Examiner* — Suzanne M Noakes
*Assistant Examiner* — Jae W Lee
(74) *Attorney, Agent, or Firm* — Pleechae IP, LLC

(57) ABSTRACT

A recombinant vector according to an embodiment of the present invention may be used for producing a reconstituted cytochrome P450 oxygenase-reductase fusion protein. Oxygenase and reductase may be independently expressed in a host cell into which the recombinant vector is introduced, and then may be fused with a split intein so that it is possible to increase the heme content contained in the active site of the oxygenase and improve enzyme activity and stability.

11 Claims, 16 Drawing Sheets

Specification includes a Sequence Listing.

Domain swapping

Hybrid library

SEQUENCE LISTING

```
<160> NUMBER OF SEQ ID NOS: 19

<210> SEQ ID NO 1
<211> LENGTH: 466
<212> TYPE: PRT
<213> ORGANISM: Bacillus megaterium

<400> SEQUENCE: 1

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Leu
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Val Arg
65                  70                  75                  80

Asp Phe Ala Gly Asp Gly Leu Val Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Pro Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Gln Gln Arg Ala
            180                 185                 190

Asn Pro Asp Asp Pro Ala Tyr Asp Glu Asn Lys Arg Gln Phe Gln Glu
        195                 200                 205

Asp Ile Lys Val Met Asn Asp Leu Val Asp Lys Ile Ile Ala Asp Arg
    210                 215                 220

Lys Ala Ser Gly Glu Gln Ser Asp Asp Leu Leu Thr His Met Leu Asn
225                 230                 235                 240
```

```
Gly Lys Asp Pro Glu Thr Gly Glu Pro Leu Asp Asp Glu Asn Ile Arg
            245                 250                 255

Tyr Gln Ile Ile Thr Phe Leu Ile Ala Gly His Glu Thr Thr Ser Gly
        260                 265                 270

Leu Leu Ser Phe Ala Leu Tyr Phe Leu Val Lys Asn Pro His Val Leu
    275                 280                 285

Gln Lys Ala Ala Glu Glu Ala Ala Arg Val Leu Val Asp Pro Val Pro
290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
            340                 345                 350

Glu Leu Met Val Leu Ile Pro Gln Leu His Arg Asp Lys Thr Ile Trp
        355                 360                 365

Gly Asp Asp Val Glu Glu Phe Arg Pro Glu Arg Phe Glu Asn Pro Ser
    370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
        435                 440                 445

Ala Lys Ser Lys Lys Ile Pro Leu Gly Gly Ile Pro Ser Pro Ser Thr
    450                 455                 460

Glu Gln
465

<210> SEQ ID NO 2
<211> LENGTH: 583
<212> TYPE: PRT
<213> ORGANISM: Bacillus megaterium

<400> SEQUENCE: 2

Ser Ala Lys Lys Val Arg Lys Lys Ala Glu Asn Ala His Asn Thr Pro
1               5                   10                  15

Leu Leu Val Leu Tyr Gly Ser Asn Met Gly Thr Ala Glu Gly Thr Ala
            20                  25                  30

Arg Asp Leu Ala Asp Ile Ala Met Ser Lys Gly Phe Ala Pro Gln Val
        35                  40                  45

Ala Thr Leu Asp Ser His Ala Gly Asn Leu Pro Arg Glu Gly Ala Val
    50                  55                  60

Leu Ile Val Thr Ala Ser Tyr Asn Gly His Pro Pro Asp Asn Ala Lys
65                  70                  75                  80

Gln Phe Val Asp Trp Leu Asp Gln Ala Ser Ala Asp Glu Val Lys Gly
                85                  90                  95

Val Arg Tyr Ser Val Phe Gly Cys Gly Asp Lys Asn Trp Ala Thr Thr
            100                 105                 110

Tyr Gln Lys Val Pro Ala Phe Ile Asp Glu Thr Leu Ala Ala Lys Gly
        115                 120                 125

Ala Glu Asn Ile Ala Asp Arg Gly Glu Ala Asp Ala Ser Asp Asp Phe
    130                 135                 140
```

```
Glu Gly Thr Tyr Glu Glu Trp Arg Glu His Met Trp Ser Asp Val Ala
145                 150                 155                 160

Ala Tyr Phe Asn Leu Asp Ile Glu Asn Ser Glu Asp Asn Lys Ser Thr
                165                 170                 175

Leu Ser Leu Gln Phe Val Asp Ser Ala Ala Asp Met Pro Leu Ala Lys
            180                 185                 190

Met His Gly Ala Phe Ser Thr Asn Val Val Ala Ser Lys Glu Leu Gln
        195                 200                 205

Gln Pro Gly Ser Ala Arg Ser Thr Arg His Leu Glu Ile Glu Leu Pro
    210                 215                 220

Lys Glu Ala Ser Tyr Gln Glu Gly Asp His Leu Gly Val Ile Pro Arg
225                 230                 235                 240

Asn Tyr Glu Gly Ile Val Asn Arg Val Thr Ala Arg Phe Gly Leu Asp
                245                 250                 255

Ala Ser Gln Gln Ile Arg Leu Glu Ala Glu Glu Lys Leu Ala His
                260                 265                 270

Leu Pro Leu Ala Lys Thr Val Ser Val Glu Glu Leu Leu Gln Tyr Val
        275                 280                 285

Glu Leu Gln Asp Pro Val Thr Arg Thr Gln Leu Arg Ala Met Ala Ala
290                 295                 300

Lys Thr Val Cys Pro Pro His Lys Val Glu Leu Glu Ala Leu Leu Glu
305                 310                 315                 320

Lys Gln Ala Tyr Lys Glu Gln Val Leu Ala Lys Arg Leu Thr Met Leu
                325                 330                 335

Glu Leu Leu Glu Lys Tyr Pro Ala Cys Glu Met Lys Phe Ser Glu Phe
            340                 345                 350

Ile Ala Leu Leu Pro Ser Ile Arg Pro Arg Tyr Tyr Ser Ile Ser Ser
        355                 360                 365

Ser Pro Arg Val Asp Glu Lys Gln Ala Ser Ile Thr Val Ser Val Val
    370                 375                 380

Ser Gly Glu Ala Trp Ser Gly Tyr Gly Glu Tyr Lys Gly Ile Ala Ser
385                 390                 395                 400

Asn Tyr Leu Ala Glu Leu Gln Glu Gly Asp Thr Ile Thr Cys Phe Ile
                405                 410                 415

Ser Thr Pro Gln Ser Glu Phe Thr Leu Pro Lys Asp Pro Glu Thr Pro
            420                 425                 430

Leu Ile Met Val Gly Pro Gly Thr Gly Val Ala Pro Phe Arg Gly Phe
        435                 440                 445

Val Gln Ala Arg Lys Gln Leu Lys Glu Gln Gly Gln Ser Leu Gly Glu
    450                 455                 460

Ala His Leu Tyr Phe Gly Cys Arg Ser Pro His Glu Asp Tyr Leu Tyr
465                 470                 475                 480

Gln Glu Glu Leu Glu Asn Ala Gln Ser Glu Gly Ile Ile Thr Leu His
                485                 490                 495

Thr Ala Phe Ser Arg Met Pro Asn Gln Pro Lys Thr Tyr Val Gln His
            500                 505                 510

Val Met Glu Gln Asp Gly Lys Lys Leu Ile Glu Leu Leu Asp Gln Gly
        515                 520                 525

Ala His Phe Tyr Ile Cys Gly Asp Gly Ser Gln Met Ala Pro Ala Val
    530                 535                 540

Glu Ala Thr Leu Met Lys Ser Tyr Ala Asp Val His Gln Val Ser Glu
545                 550                 555                 560
```

Ala Asp Ala Arg Leu Trp Leu Gln Gln Leu Glu Glu Lys Gly Arg Tyr
            565                 570                 575

Ala Lys Asp Val Trp Ala Gly
        580

<210> SEQ ID NO 3
<211> LENGTH: 1398
<212> TYPE: DNA
<213> ORGANISM: Bacillus megaterium

<400> SEQUENCE: 3

| | | | | | |
|---|---|---|---|---|---|
| atgacaatta | agaaatgcc | tcagccaaaa | acgtttggag | agcttaaaaa | tttaccgtta | 60 |
| ttaaacacag | ataaaccggt | tcaagctttg | atgaaaattg | cggatgaatt | aggagaaatc | 120 |
| tttaaattcg | aggcgcctgg | tctggtaacg | cgctacttat | caagtcagcg | tctaattaaa | 180 |
| gaagcatgcg | atgaatcacg | ctttgataaa | aacttaagtc | aagcgcttaa | atttgtacgt | 240 |
| gattttgcag | agacgggtt | agtgacaagc | tggacgcatg | aaaaaaattg | gaaaaaagcg | 300 |
| cataatatct | tacttccaag | cttcagtcag | caggcaatga | aaggctatca | tgcgatgatg | 360 |
| gtcgatatcg | ccgtgcagct | tgttcaaaag | tgggagcgtc | taaatgcaga | tgagcatatt | 420 |
| gaagtaccgg | aagacatgac | acgtttaacg | cttgatacaa | ttggtctttg | cggctttaac | 480 |
| tatcgcttta | acagctttta | ccgagatcag | cctcatccat | ttattacaag | tatggtccgt | 540 |
| gcactggatg | aagcaatgaa | caagcagcag | cgagcaaatc | cagacgaccc | agcttatgat | 600 |
| gaaaacaagc | gccagtttca | gaagatatc | aaggtgatga | acgacctagt | agataaaatt | 660 |
| attgcagatg | caaagcaag | cggtgaacaa | agcgatgatt | tattaacgca | tatgctaaac | 720 |
| ggaaaagatc | cagaaacggg | tgagccgctt | gatgacgaga | cattcgcta | tcaaattatt | 780 |
| acattcttaa | ttgcgggaca | cgaaacaaca | agtggtcttt | tatcatttgc | gctgtatttc | 840 |
| ttagtgaaaa | atccacatgt | attacaaaaa | gcagcagaag | aagcagcacg | agttctagta | 900 |
| gatcctgttc | caagctacaa | acaagtcaaa | cagcttaaat | atgtcggcat | ggtcttaaac | 960 |
| gaagcgctgc | gcttatggcc | aactgctcct | gcgttttccc | tatatgcaaa | agaagatacg | 1020 |
| gtgcttggag | gagaatatcc | tttagaaaaa | ggcgacgaac | taatggttct | gattcctcag | 1080 |
| cttcaccgtg | ataaaacaat | tggggagac | gatgtggaag | agttccgtcc | agagcgtttt | 1140 |
| gaaaatccaa | gtcgattcc | gcagcatgcg | tttaaaccgt | ttggaaacgg | tcagcgtgcg | 1200 |
| tgtatcggtc | agcagttcgc | tcttcatgaa | gcaacgctgg | tacttggtat | gatgctaaaa | 1260 |
| cactttgact | tgaagatca | tacaaactac | gagctcgata | ttaaagaaac | tttaacgtta | 1320 |
| aaacctgaag | gctttgtggt | aaaagcaaaa | tcgaaaaaaa | ttccgcttgg | cggtattcct | 1380 |
| tcacctagca | ctgaacag | | | | | 1398 |

<210> SEQ ID NO 4
<211> LENGTH: 1749
<212> TYPE: DNA
<213> ORGANISM: Bacillus megaterium

<400> SEQUENCE: 4

| | | | | | |
|---|---|---|---|---|---|
| tctgctaaaa | aagtacgcaa | aaaggcagaa | aacgctcata | atacgccgct | gcttgtgcta | 60 |
| tacggttcaa | atatgggaac | agctgaagga | acggcgcgtg | atttagcaga | tattgcaatg | 120 |
| agcaaaggat | ttgcaccgca | ggtcgcaacg | cttgattcac | acgccggaaa | tcttccgcgc | 180 |
| gaaggagctg | tattaattgt | aacgcgcgtct | tataacggtc | atccgcctga | taacgcaaag | 240 |
| caatttgtcg | actggttaga | ccaagcgtct | gctgatgaag | taaaaggcgt | tcgctactcc | 300 |

```
gtatttggat gcggcgataa aaactgggct actacgtatc aaaaagtgcc tgcttttatc    360
gatgaaacgc ttgccgctaa aggggcagaa acatcgctg accgcggtga agcagatgca    420
agcgacgact ttgaaggcac atatgaagaa tggcgtgaac atatgtggag tgacgtagca    480
gcctacttta acctcgacat tgaaaacagt gaagataata aatctactct ttcacttcaa    540
tttgtcgaca gcgccgcgga tatgccgctt gcgaaaatgc acggtgcgtt ttcaacgaac    600
gtcgtagcaa gcaaagaact tcaacagcca ggcagtgcac gaagcacgcg acatcttgaa    660
attgaacttc caaagaagc ttcttatcaa gaaggagatc atttaggtgt tattcctcgc     720
aactatgaag gaatagtaaa ccgtgtaaca gcaaggttcg gcctagatgc atcacagcaa    780
atccgtctgg aagcagaaga agaaaaatta gctcatttgc cactcgctaa aacagtatcc    840
gtagaagagc ttctgcaata cgtggagctt caagatcctg ttacgcgcac gcagcttcgc    900
gcaatggctg ctaaaacggt ctgcccgccg cataaagtag agcttgaagc cttgcttgaa    960
aagcaagcct acaaagaaca agtgctggca aacgtttaa caatgcttga actgcttgaa    1020
aaatacccgg cgtgtgaaat gaaattcagc gaatttatcg cccttctgcc aagcatacgc    1080
ccgcgctatt actcgatttc ttcatcacct cgtgtcgatg aaaaacaagc aagcatcacg    1140
gtcagcgttg tctcaggaga agcgtggagc ggatatgag aatataaagg aattgcgtcg     1200
aactatcttg ccgagctgca agaaggagat acgattacgt gctttatttc cacaccgcag    1260
tcagaattta cgctgccaaa agaccctgaa acgccgctta tcatggtcgg accgggaaca    1320
ggcgtcgcgc cgtttagagg ctttgtgcag gcgcgcaaac agctaaaaga caaggacag     1380 tcacttggag aagcacattt atacttcggc tgccgttcac ctcatgaaga ctatctgtat    1440
caagaagagc ttgaaaacgc ccaaagcgaa ggcatcatta cgcttcatac cgcttttct     1500 cgcatgccaa atcagccgaa aacatacgtt cagcacgtaa tggaacaaga cggcaagaaa    1560
ttgattgaac ttcttgatca aggagcgcac ttctatattt gcggagacgg aagccaaatg    1620
gcacctgccg ttgaagcaac gcttatgaaa agctatgctg acgttcacca agtgagtgaa    1680
gcagacgctc gcttatggct gcagcagcta aagaaaaag gccgatacgc aaaagacgtg     1740
tgggctggg                                                           1749
```

<210> SEQ ID NO 5
<211> LENGTH: 478
<212> TYPE: DNA
<213> ORGANISM: Artificial Sequence
<220> FEATURE:
<223> OTHER INFORMATION: split intein

<400> SEQUENCE: 5

```
gctagcgcga ctaaatgtct gagctatgaa accgagattt taacggttga gtacggactg     60
ctcccaatcg gtaaaattgt tgaaaagcgc atcgaatgca cggtctacag cgtcgataac    120
aatggcaaca tttatacaca gcctgtagca cagtggcacg atcggggcga gcaagaggtg    180
tttgaatatt gccttgagga tggtagcctg atacgtgcca caaaagacca taaatttatg    240
accgtggatg ggcagatgct gccgattgat gagatcttcg aacgtgaact ggacttgatg    300
cgcgttgaca atctgcccaa tggatcctaa tgaggaggtt taaatatgg agctcatcaa     360 aattgcgacc cgcaagtatc tgggcaagca gaacgtgtac gatattgggg tggaacgcga    420
ccataacttt gccctgaaaa acggttcat cgcaagcaac tgctttaaca agactagt       478
```

<210> SEQ ID NO 6

```
<211> LENGTH: 154
<212> TYPE: PRT
<213> ORGANISM: Artificial Sequence
<220> FEATURE:
<223> OTHER INFORMATION: split intein

<400> SEQUENCE: 6

Ala Ser Ala Thr Lys Cys Leu Ser Tyr Glu Thr Glu Ile Leu Thr Val
1               5                   10                  15

Glu Tyr Gly Leu Leu Pro Ile Gly Lys Ile Val Glu Lys Arg Ile Glu
            20                  25                  30

Cys Thr Val Tyr Ser Val Asp Asn Asn Gly Asn Ile Tyr Thr Gln Pro
        35                  40                  45

Val Ala Gln Trp His Asp Arg Gly Glu Gln Glu Val Phe Glu Tyr Cys
    50                  55                  60

Leu Glu Asp Gly Ser Leu Ile Arg Ala Thr Lys Asp His Lys Phe Met
65                  70                  75                  80

Thr Val Asp Gly Gln Met Leu Pro Ile Asp Glu Ile Phe Glu Arg Glu
                85                  90                  95

Leu Asp Leu Met Arg Val Asp Asn Leu Pro Asn Gly Ser Gly Gly Leu
            100                 105                 110

Lys Tyr Gly Ala His Gln Asn Cys Asp Pro Gln Val Ser Gly Gln Ala
        115                 120                 125

Glu Arg Val Arg Tyr Trp Gly Gly Thr Arg Pro Leu Cys Pro Glu Lys
    130                 135                 140

Arg Phe His Arg Lys Gln Leu Leu Gln Asp
145                 150

<210> SEQ ID NO 7
<211> LENGTH: 3646
<212> TYPE: DNA
<213> ORGANISM: Artificial Sequence
<220> FEATURE:
<223> OTHER INFORMATION: oxygenase-split intein-reductase

<400> SEQUENCE: 7
atgacaatta aagaaatgcc tcagccaaaa acgtttggag agcttaaaaa tttaccgtta      60
ttaaacacag ataaaccggt tcaagctttg atgaaaattg cggatgaatt aggagaaatc     120
tttaaattcg aggcgcctgg tcgtgtaacg cgctacttat caagtcagcg tctaattaaa     180
gaagcatgcg atgaatcacg ctttgataaa aacttaagtc aagcgcttaa atttgtacgt     240
gattttgcag agacgggttt atttacaagc tggacgcatg aaaaaaattg gaaaaaagcg     300
cataatatct tacttccaag cttcagtcag caggcaatga aaggctatca tgcgatgatg     360
gtcgatatcg ccgtgcagct tgttcaaaag tgggagcgtc taaatgcaga tgagcatatt     420
gaagtaccgg aagacatgac acgtttaacg cttgatacaa ttggtctttg cggctttaac     480
tatcgcttta caagctttta ccgagatcag cctcatccat ttattacaag tatggtccgt     540
gcactggatg aagcaatgaa caagctgcag cgagcaaatc cagacgaccc agcttatgat     600
gaaaacaagc gccagtttca gaagatatcc aaggtgatga cgacctagta gataaaatt      660 attgcagatc gcaaagcaag cggtgaacaa agcgatgatt tattaacgca tatgctaaac     720
ggaaaagatc cagaaacggg tgagccgctt gatgacgaga cattcgcta tcaaattatt      780 acattcttaa ttgcgggaca cgaaacaaca agtggtcttt tatcatttgc gctgtatttc     840
ttagtgaaaa atccacatgt attacaaaaa gcagcagaag aagcagcacg agttctagta     900
gatcctgttc caagctacaa acaagtcaaa cagcttaaat atgtcggcat ggtcttaaac     960
```

```
gaagcgctgc gcttatggcc aactgctcct gcgttttccc tatatgcaaa agaagatacg    1020
gtgcttggag gagaatatcc tttagaaaaa ggcgacgaac taatggttct gattcctcag    1080
cttcaccgtg ataaaacaat ttggggagac gatgtggaag agttccgtcc agagcgtttt    1140
gaaaatccaa gtgcgattcc gcagcatgcg tttaaaccgt ttggaaacgg tcagcgtgcg    1200
tgtatcggtc agcagttcgc tcttcatgaa gcaacgctgg tacttggtat gatgctaaaa    1260
cactttgact ttgaagatca tacaaactac gagctcgata ttaaagaaac tttaacgtta    1320
aaacctgaag gctttgtggt aaaagcaaaa tcgaaaaaaa ttccgcttgg cggtattcct    1380
tcacctagca ctgaacaggc tagcgcgact aaatgtctga gctatgaaac cgagatttta    1440
acggttgagt acggactgct cccaatcggt aaaattgttg aaaagcgcat cgaatgcacg    1500
gtctacagcg tcgataacaa tggcaacatt tatacacagc ctgtagcaca gtggcacgat    1560
cggggcgagc aagaggtgtt tgaatattgc cttgaggatg gtagcctgat acgtgccaca    1620
aaagaccata aatttatgac cgtggatggg cagatgctgc cgattgatga gatcttcgaa    1680
cgtgaactgg acttgatgcg cgttgacaat ctgcccaatg gatcctaatg aggaggttta    1740
aaatatggag ctcatcaaaa ttgcgacccg caagtatctg ggcaagcaga acgtgtacga    1800
tattggggtg gaacgcgacc ataactttgc cctgaaaaac ggtttcatcg caagcaactg    1860
ctttaacaag actagttctg ctaaaaaagt acgcaaaaag gcagaaaacg ctcataatac    1920
gccgctgctt gtgctatacg gttcaaatat gggaacagct gaaggaacgg cgcgtgattt    1980
agcagatatt gcaatgagca aaggatttgc accgcaggtc gcaacgcttg attcacacgc    2040
cggaaatctt ccgcgcgaag gagctgtatt aattgtaacg gcgtcttata acggtcatcc    2100
gcctgataac gcaaagcaat tgtcgactg gttagaccaa gcgtctgctg atgaagtaaa    2160
aggcgttcgc tactccgtat ttggatgcgg cgataaaaac tgggctacta cgtatcaaaa    2220
agtgcctgct tttatcgatg aaacgcttgc cgctaaaggg gcagaaaaca tcgctgaccg    2280
cggtgaagca gatgcaagcg acgactttga aggcacatat gaagaatggc gtgaacatat    2340
gtggagtgac gtagcagcct actttaacct cgacattgaa aacagtgaag ataataaatc    2400
tactcttcca cttcaatttg tcgacagcgc cgcggatatg ccgcttgcga aaatgcacgg    2460
tgcgttttca acgaacgtcg tagcaagcaa agaacttcaa cagccaggca gtgcacgaag    2520
cacgcgacat cttgaaattg aacttccaaa agaagcttct tatcaagaag gagatcattt    2580
aggtgttatt cctcgcaact atgaaggaat agtaaaccgt gtaacagcaa ggttcggcct    2640
agatgcatca cagcaaatcc gtctggaagc agaagaagaa aaattagctc atttgccact    2700
cgctaaaaca gtatccgtag aagagcttct gcaatacgtg gagcttcaag atcctgttac    2760
gcgcacgcaa cttcgcgcaa tggctgctaa aacggtctgc ccgccgcata agtagagct    2820 tgaagccttg cttgaaaagc aagcctacaa agaacaagtg ctggcaaaac gtttaacaat    2880
gcttgaactg cttgaaaaat acccggcgtg tgaaatgaaa ttcagcgaat ttatcgccct    2940
tctgccaagc atacgcccgc gctattactc gatttcttca tcacctcgtg tcgatgaaaa    3000
acaagcaagc atcacggtca gcgttgtctc aggagaagcg tggagcggat atggagaata    3060
taaaggaatt gcgtcgaact atcttgccga gctgcaagaa ggagatacga ttacgtgctt    3120
tatttccaca ccgcagtcag aatttacgct gccaaaagac cctgaaacgc cgcttatcat    3180
ggtcggaccg ggaacaggcg tcgcgccgtt tagaggcttt gtgcaggcgc gcaaacagct    3240
aaaagaacaa ggacagtcac ttggagaagc acatttatac ttcggctgcc gttcacctca    3300
```

```
tgaagactat ctgtatcaag aagagcttga aaacgcccaa agcgaaggca tcattacgct    3360
tcataccgct ttttctcgca tgccaaatca gccgaaaaca tacgttcagc acgtaatgga    3420
acaagacggc aagaaattga ttgaacttct tgatcaagga gcgcacttct atatttgcgg    3480
agacggaagc caaatggcac ctgccgttga agcaacgctt atgaaaagct atgctgacgt    3540
tcaccaagtg agtgaagcag acgctcgctt atggctgcag cagctagaag aaaaaggccg    3600
atacgcaaaa gacgtgtggg ctgggcatca ccatcaccat cactaa                   3646
```

<210> SEQ ID NO 8
<211> LENGTH: 1063
<212> TYPE: PRT
<213> ORGANISM: Bacillus megaterium

<400> SEQUENCE: 8

```
Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Val Arg
65                  70                  75                  80

Asp Phe Ala Gly Asp Gly Leu Phe Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Pro Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
            180                 185                 190

Asn Pro Asp Asp Pro Ala Tyr Asp Glu Asn Lys Arg Gln Phe Gln Glu
        195                 200                 205

Asp Ile Lys Val Met Asn Asp Leu Val Asp Lys Ile Ala Asp Arg
    210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Ala Ala Glu Glu Ala Ala Arg Val Leu Val Asp Pro Val Pro
    290                 295                 300

Ser Tyr Lys Gln Val Lys Gln Leu Lys Tyr Val Gly Met Val Leu Asn
305                 310                 315                 320
```

```
Glu Ala Leu Arg Leu Trp Pro Thr Ala Pro Ala Phe Ser Leu Tyr Ala
            325                 330                 335

Lys Glu Asp Thr Val Leu Gly Gly Glu Tyr Pro Leu Glu Lys Gly Asp
        340                 345                 350

Glu Leu Met Val Leu Ile Pro Gln Leu His Arg Asp Lys Thr Ile Trp
    355                 360                 365

Gly Asp Asp Val Glu Glu Phe Arg Pro Glu Arg Phe Glu Asn Pro Ser
370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
        435                 440                 445

Ala Lys Ser Lys Lys Ile Pro Leu Gly Gly Ile Pro Ser Pro Ser Thr
    450                 455                 460

Glu Gln Ala Ser Cys Phe Asn Lys Thr Ser Ser Ala Lys Lys Val Arg
465                 470                 475                 480

Lys Lys Ala Glu Asn Ala His Asn Thr Pro Leu Leu Val Leu Tyr Gly
                485                 490                 495

Ser Asn Met Gly Thr Ala Glu Gly Thr Ala Arg Asp Leu Ala Asp Ile
            500                 505                 510

Ala Met Ser Lys Gly Phe Ala Pro Gln Val Ala Thr Leu Asp Ser His
        515                 520                 525

Ala Gly Asn Leu Pro Arg Glu Gly Ala Val Leu Ile Val Thr Ala Ser
    530                 535                 540

Tyr Asn Gly His Pro Pro Asp Asn Ala Lys Gln Phe Val Asp Trp Leu
545                 550                 555                 560

Asp Gln Ala Ser Ala Asp Glu Val Lys Gly Val Arg Tyr Ser Val Phe
                565                 570                 575

Gly Cys Gly Asp Lys Asn Trp Ala Thr Thr Tyr Gln Lys Val Pro Ala
            580                 585                 590

Phe Ile Asp Glu Thr Leu Ala Ala Lys Gly Ala Glu Asn Ile Ala Asp
        595                 600                 605

Arg Gly Glu Ala Asp Ala Ser Asp Asp Phe Glu Gly Thr Tyr Glu Glu
    610                 615                 620

Trp Arg Glu His Met Trp Ser Asp Val Ala Ala Tyr Phe Asn Leu Asp
625                 630                 635                 640

Ile Glu Asn Ser Glu Asp Asn Lys Ser Thr Leu Ser Leu Gln Phe Val
                645                 650                 655

Asp Ser Ala Ala Asp Met Pro Leu Ala Lys Met His Gly Ala Phe Ser
            660                 665                 670

Thr Asn Val Val Ala Ser Lys Glu Leu Gln Gln Pro Gly Ser Ala Arg
        675                 680                 685

Ser Thr Arg His Leu Glu Ile Glu Leu Pro Lys Glu Ala Ser Tyr Gln
    690                 695                 700

Glu Gly Asp His Leu Gly Val Ile Pro Arg Asn Tyr Glu Gly Ile Val
705                 710                 715                 720

Asn Arg Val Thr Ala Arg Phe Gly Leu Asp Ala Ser Gln Gln Ile Arg
                725                 730                 735
```

-continued

Leu Glu Ala Glu Glu Lys Leu Ala His Leu Pro Leu Ala Lys Thr
          740                 745                 750
Val Ser Val Glu Glu Leu Leu Gln Tyr Val Glu Leu Gln Asp Pro Val
      755                 760                 765
Thr Arg Thr Gln Leu Arg Ala Met Ala Ala Lys Thr Val Cys Pro Pro
  770                 775                 780
His Lys Val Glu Leu Glu Ala Leu Leu Glu Lys Gln Ala Tyr Lys Glu
785                 790                 795                 800
Gln Val Leu Ala Lys Arg Leu Thr Met Leu Glu Leu Leu Glu Lys Tyr
              805                 810                 815
Pro Ala Cys Glu Met Lys Phe Ser Glu Phe Ile Ala Leu Leu Pro Ser
          820                 825                 830
Ile Arg Pro Arg Tyr Tyr Ser Ile Ser Ser Ser Pro Arg Val Asp Glu
      835                 840                 845
Lys Gln Ala Ser Ile Thr Val Ser Val Val Ser Gly Glu Ala Trp Ser
  850                 855                 860
Gly Tyr Gly Glu Tyr Lys Gly Ile Ala Ser Asn Tyr Leu Ala Glu Leu
865                 870                 875                 880
Gln Glu Gly Asp Thr Ile Thr Cys Phe Ile Ser Thr Pro Gln Ser Glu
              885                 890                 895
Phe Thr Leu Pro Lys Asp Pro Glu Thr Pro Leu Ile Met Val Gly Pro
          900                 905                 910
Gly Thr Gly Val Ala Pro Phe Arg Gly Phe Val Gln Ala Arg Lys Gln
      915                 920                 925
Leu Lys Glu Gln Gly Gln Ser Leu Gly Glu Ala His Leu Tyr Phe Gly
  930                 935                 940
Cys Arg Ser Pro His Glu Asp Tyr Leu Tyr Gln Glu Glu Leu Glu Asn
945                 950                 955                 960
Ala Gln Ser Glu Gly Ile Ile Thr Leu His Thr Ala Phe Ser Arg Met
              965                 970                 975
Pro Asn Gln Pro Lys Thr Tyr Val Gln His Val Met Glu Gln Asp Gly
          980                 985                 990
Lys Lys Leu Ile Glu Leu Leu Asp Gln Gly Ala His Phe Tyr Ile Cys
      995                 1000                1005
Gly Asp Gly Ser Gln Met Ala Pro Ala Val Glu Ala Thr Leu Met
  1010                1015                1020
Lys Ser Tyr Ala Asp Val His Gln Val Ser Glu Ala Asp Ala Arg
  1025                1030                1035
Leu Trp Leu Gln Gln Leu Glu Glu Lys Gly Arg Tyr Ala Lys Asp
  1040                1045                1050
Val Trp Ala Gly His His His His His His
  1055                1060

<210> SEQ ID NO 9
<211> LENGTH: 38
<212> TYPE: DNA
<213> ORGANISM: Artificial Sequence
<220> FEATURE:
<223> OTHER INFORMATION: BM3_#10 F

<400> SEQUENCE: 9
ggagatatac atatgacaat taaagaaatg cctcagcc                           38

<210> SEQ ID NO 10
<211> LENGTH: 51
<212> TYPE: DNA

<210> SEQ ID NO 11
<211> LENGTH: 59
<212> TYPE: DNA
<213> ORGANISM: Artificial Sequence
<220> FEATURE:
<223> OTHER INFORMATION: BM3_#10 R

<400> SEQUENCE: 10
acggagctcg aattcttagt gatggtgatg gtgatgccca gcccacacgt c        51

<210> SEQ ID NO 11
<211> LENGTH: 59
<212> TYPE: DNA
<213> ORGANISM: Artificial Sequence
<220> FEATURE:
<223> OTHER INFORMATION: OXI INFUSION F

<400> SEQUENCE: 11
taacaattcc cctctagaaa taattttgtt taactttaag aaggagatat acatatgac    59

<210> SEQ ID NO 12
<211> LENGTH: 31
<212> TYPE: DNA
<213> ORGANISM: Artificial Sequence
<220> FEATURE:
<223> OTHER INFORMATION: OXI OVERLAP R

<400> SEQUENCE: 12
gtacagctag cctgttcagt gctaggtgaa g        31

<210> SEQ ID NO 13
<211> LENGTH: 36
<212> TYPE: DNA
<213> ORGANISM: Artificial Sequence
<220> FEATURE:
<223> OTHER INFORMATION: RE OVERLAP F

<400> SEQUENCE: 13
caagactagt tctgctaaaa aagtacgcaa aaaggc        36

<210> SEQ ID NO 14
<211> LENGTH: 44
<212> TYPE: DNA
<213> ORGANISM: Artificial Sequence
<220> FEATURE:
<223> OTHER INFORMATION: RE INFUSION R

<400> SEQUENCE: 14
tcgacggagc tcgaattctt agtgatggtg atggtgatgc ccag        44

<210> SEQ ID NO 15
<211> LENGTH: 43
<212> TYPE: DNA
<213> ORGANISM: Artificial Sequence
<220> FEATURE:
<223> OTHER INFORMATION: INTEIN OVERLAP F

<400> SEQUENCE: 15
cactgaacag gctagctgta ctaaatgtct gagctatgaa acc        43

<210> SEQ ID NO 16
<211> LENGTH: 45
<212> TYPE: DNA
<213> ORGANISM: Artificial Sequence
<220> FEATURE:
<223> OTHER INFORMATION: INTEIN INFUSION R

<400> SEQUENCE: 16
gcgtactttt ttagcagaac tagtcttgtt aaagcagttg cttgc        45

<210> SEQ ID NO 17
<211> LENGTH: 3150
<212> TYPE: DNA
<213> ORGANISM: Artificial Sequence
<220> FEATURE:
<223> OTHER INFORMATION: pET24a-oxygenase-reductase

<400> SEQUENCE: 17

```
atgacaatta agaaatgcc tcagccaaaa acgtttggag agcttaaaaa tttaccgtta      60
ttaaacacag ataaaccggt tcaagctttg atgaaaattg cggatgaatt aggagaaatc    120
tttaaattcg aggcgcctgg tcgtgtaacg cgctacttat caagtcagcg tctaattaaa    180
gaagcatgcg atgaatcacg ctttgataaa aacttaagtc aagcgcttaa atttgtacgt    240
gattttgcag agacggggtt atttacaagc tggacgcatg aaaaaaattg gaaaaaagcg    300
cataatatct tacttccaag cttcagtcag caggcaatga aaggctatca tgcgatgatg    360
gtcgatatcg ccgtgcagct tgttcaaaag tgggagcgtc taaatgcaga tgagcatatt    420
gaagtaccgg aagacatgac acgtttaacg cttgatacaa ttggtctttg cggctttaac    480
tatcgcttta acagctttta ccgagatcag cctcatccat ttattacaag tatggtccgt    540
gcactggatg aagcaatgaa caagctgcag cgagcaaatc cagacgaccc agcttatgat    600
gaaacaagc gccagtttca agaagatatc aaggtgatga cgacctagt agataaaatt    660
attgcagatc gcaaagcaag cggtgaacaa agcgatgatt tattaacgca tatgctaaac    720
ggaaaagatc cagaaacggg tgagccgctt gatgacgaga acattcgcta tcaaattatt    780
acattcttaa ttgcgggaca cgaaacaaca agtggtcttt tatcatttgc gctgtatttc    840
ttagtgaaaa atccacatgt attacaaaaa gcagcagaag aagcagcacg agttctagta    900
gatcctgttc aagctacaa acaagtcaaa cagcttaaat atgtcggcat ggtcttaaac    960
gaagcgctgc gcttatggcc aactgctcct gcgttttccc tatatgcaaa agaagatacg   1020
gtgcttggag gagaatatcc tttagaaaaa ggcgacgaac taatggttct gattcctcag   1080
cttcaccgtg ataaaacaat tggggagac gatgtggaag agttccgtcc agagcgtttt   1140
gaaaatccaa gtgcgattcc gcagcatgcg tttaaaccgt ttggaaacgg tcagcgtgcg   1200
tgtatcggtc agcagttcgc tcttcatgaa gcaacgctgg tacttggtat gatgctaaaa   1260
cactttgact ttgaagatca tacaaactac gagctcgata ttaaagaaac tttaacgtta   1320
aaacctgaag gctttgtggt aaaagcaaaa tcgaaaaaaa ttccgcttgg cggtattcct   1380
tcacctagca ctgaacagtc tgctaaaaaa gtacgcaaaa aggcagaaaa cgctcataat   1440
acgccgctgc ttgtgctata cggttcaaat atgggaacag ctgaaggaac ggcgcgtgat   1500
ttagcagata ttgcaatgag caaaggattt gcaccgcagg tcgcaacgct tgattcacac   1560
gccggaaatc ttccgcgcga aggagctgta ttaattgtaa cggcgtctta taacggtcat   1620
ccgcctgata acgcaaagca attttgtcga ctggttagacc aagcgtctgc tgatgaagta   1680
aaaggcgttc gctactccgt atttggatgc ggcgataaaa actgggctac tacgtatcaa   1740
aaagtgcctg cttttatcga tgaaacgctt gccgctaaag gggcagaaaa catcgctgac   1800
cgcggtgaag cagatgcaag cgacgacttt gaaggcacat atgaagaatg cgtgaacat   1860
atgtggagtg acgtagcagc ctactttaac ctcgacattg aaaacagtga agataataaa   1920
tctactcttt cacttcaatt tgtcgacagc gccgcgata tgccgcttgc gaaaatgcac   1980
ggtgcgtttt caacgaacgt cgtagcaagc aaagaacttc aacagccagg cagtgcacga   2040
```

```
agcacgcgac atcttgaaat tgaacttcca aaagaagctt cttatcaaga aggagatcat    2100
ttaggtgtta ttcctcgcaa ctatgaagga atagtaaacc gtgtaacagc aaggttcggc    2160
ctagatgcat cacagcaaat ccgtctggaa gcagaagaag aaaaattagc tcatttgcca    2220
ctcgctaaaa cagtatccgt agaagagctt ctgcaatacg tggagcttca agatcctgtt    2280
acgcgcacgc agcttcgcgc aatggctgct aaaacggtct gcccgccgca taagtagag    2340
cttgaagcct tgcttgaaaa gcaagcctac aaagaacaag tgctggcaaa acgtttaaca    2400
atgcttgaac tgcttgaaaa ataccccggcg tgtgaaatga aattcagcga atttatcgcc    2460
cttctgccaa gcatacgccc cgcgtattac tcgatttctt catcacctcg tgtcgatgaa    2520
aaacaagcaa gcatcacggt cagcgttgtc tcaggagaag cgtggagcgg atatggagaa    2580
tataaaggaa ttgcgtcgaa ctatcttgcc gagctgcaag aaggagatac gattacgtgc    2640
tttatttcca caccgcagtc agaatttacg ctgccaaaag accctgaaac gccgcttatc    2700
atggtcggac cgggaacagg cgtcgcgccg tttagaggct ttgtgcaggc gcgcaaacag    2760
ctaaaagaac aaggacagtc acttggagaa gcacatttat acttcggctg ccgttcacct    2820
catgaagact atctgtatca agaagagctt gaaaacgccc aaagcgaagg catcattacg    2880
cttcataccg cttttctcg catgccaaat cagccgaaaa catacgttca gcacgtaatg    2940
gaacaagacg gcaagaaatt gattgaactt cttgatcaag gagcgcactt ctatatttgc    3000
ggagacggaa gccaaatggc acctgccgtt gaagcaacgc ttatgaaaag ctatgctgac    3060
gttcaccaag tgagtgaagc agacgctcgc ttatggctgc agcagctaga agaaaaaggc    3120
cgatacgcaa aagacgtgtg ggctgggtaa                                      3150

<210> SEQ ID NO 18
<211> LENGTH: 3192
<212> TYPE: DNA
<213> ORGANISM: Bacillus megaterium

<400> SEQUENCE: 18
atgacaatta aagaaatgcc tcagccaaaa acgtttggag agcttaaaaa tttaccgtta     60
ttaaacacag ataaaccggt tcaagctttg atgaaaattg cggatgaatt aggagaaatc    120
tttaaattcg aggcgcctgg tctggtaacg cgctacttat caagtcagcg tctaattaaa    180
gaagcatgcg atgaatcacg ctttgataaa aacttaagtc aagcgcttaa atttgtacgt    240
gattttgcag gagacgggtt agtgacaagc tggacgcatg aaaaaaattg gaaaaaagcg    300
cataatatct tacttccaag cttcagtcag caggcaatga aaggctatca tgcgatgatg    360
gtcgatatcg ccgtgcagct tgttcaaaag tgggagcgtc taaatgcaga tgagcatatt    420
gaagtaccgg aagacatgac acgtttaacg cttgatacaa ttggtctttg cggctttaac    480
tatcgcttta acagctttta ccgagatcag cctcatccat ttattacaag tatggtccgt    540
gcactggatg aagcaatgaa caagcagcag cgagcaaatc cagacgaccc agcttatgat    600
gaaaacaagc gccagtttca agaagatatc aaggtgatga cgacctagt agataaaatt    660
attgcagatc gcaaagcaag cggtgaacaa agcgatgatt tattaacgca tatgctaaac    720
ggaaaagatc cagaaacggg tgagccgctt gatgacgaga acattcgcta tcaaattatt    780
acattcttaa ttgcgggaca cgaaacaaca agtggtcttt tatcatttgc gctgtatttc    840
ttagtgaaaa atccacatgt attacaaaaa gcagcagaag aagcagcacg agttctagta    900
gatcctgttc aagctacaa acaagtcaaa cagcttaaat atgtcggcat ggtcttaaac    960
gaagcgctgc gcttatggcc aactgctcct gcgttttccc tatatgcaaa agaagatacg   1020
```

```
gtgcttggag gagaatatcc tttagaaaaa ggcgacgaac taatggttct gattcctcag    1080
cttcaccgtg ataaaacaat tggggagac atgtgtgaag agttccgtcc agagcgtttt    1140
gaaaatccaa gtgcgattcc gcagcatgcg tttaaaccgt ttggaaacgg tcagcgtgcg    1200
tgtatcggtc agcagttcgc tcttcatgaa gcaacgctgg tacttggtat gatgctaaaa    1260
cactttgact ttgaagatca tacaaactac gagctcgata ttaaagaaac tttaacgtta    1320
aaacctgaag gctttgtggt aaaagcaaaa tcgaaaaaaa ttccgcttgg cggtattcct    1380
tcacctagca ctgaacaggc tagctgcttt aacaagacta gttctgctaa aaaagtacgc    1440
aaaaaggcag aaaacgctca taatacgccg ctgcttgtgc tatacggttc aaatatggga    1500
acagctgaag gaacggcgcg tgatttagca gatattgcaa tgagcaaagg atttgcaccg    1560
caggtcgcaa cgcttgattc acacgccgga atcttccgc gcgaaggagc tgtattaatt    1620
gtaacggcgt cttataacgg tcatccgcct gataacgcaa agcaatttgt cgactggtta    1680
gaccaagcgt ctgctgatga gtaaaaaggc gttcgctact ccgtatttgg atgcggcgat    1740
aaaaactggg ctactacgta tcaaaaagtg cctgcttta tcgatgaaac gcttgccgct    1800
aaaggggcag aaaacatcgc tgaccgcggt gaagcagatg caagcgacga ctttgaaggc    1860
acatatgaag aatggcgtga acatatgtgg agtgacgtag cagcctactt taacctcgac    1920
attgaaaaca gtgaagataa taaatctact cttttcacttc aatttgtcga cagcgccgcg    1980
gatatgccgc ttgcgaaaat gcacggtgcg ttttcaacga acgtcgtagc aagcaaagaa    2040
cttcaacagc caggcagtgc acgaagcacg cgacatcttg aaattgaact tccaaaagaa    2100
gcttcttatc aagaaggaga tcatttaggt gttattcctc gcaactatga aggaatagta    2160
aaccgtgtaa cagcaaggtt cggcctagat gcatcacagc aaatccgtct ggaagcagaa    2220
gaagaaaaat tagctcattt gccactcgct aaaacagtat ccgtagaaga gcttctgcaa    2280
tacgtggagc ttcaagatcc tgttacgcgc acgcagcttc gcgcaatggc tgctaaaacg    2340
gtctgcccgc cgcataaagt agagcttgaa gccttgcttg aaaagcaagc ctacaaagaa    2400
caagtgctgg caaaacgttt taacaatgct gaactgcttg aaaaatac cc ggcgtgtgaa    2460 atgaaattca gcgaatttat cgcccttctg ccaagcatac gcccgcgcta ttactcgatt    2520
tcttcatcac ctcgtgtcga tgaaaaacaa gcaagcatca cggtcagcgt tgtctcagga    2580
gaagcgtgga gcggatatgg agaatataaa ggaattgcgt cgaactatct tgccgagctg    2640
caagaaggag atacgattac gtgctttatt tccacaccgc agtcagaatt tacgctgcca    2700
aaagaccctg aaacgccgct tatcatggtc ggaccgggaa caggcgtcgc gccgtttaga    2760
ggctttgtgc aggcgcgcaa acagctaaaa gaacaaggac agtcacttgg agaagcacat    2820
ttatacttcg gctgccgttc acctcatgaa gactatctgt atcaagaaga gcttgaaaac    2880
gcccaaagcg aaggcatcat tacgcttcat accgcttttt ctcgcatgcc aaatcagccg    2940
aaaacatacg ttcagcacgt aatggaacaa gacggcaaga aattgattga acttcttgat    3000
caaggagcgc acttctatat ttgcggagac ggaagccaaa tggcacctgc cgttgaagca    3060
acgcttatga aaagctatgc tgacgttcac caagtgagtg aagcagacgc tcgcttatgg    3120
ctgcagcagc tagaagaaaa aggccgatac gcaaaagacg tgtgggctgg gcatcaccat    3180
caccatcact aa                                                        3192
```

<210> SEQ ID NO 19
<211> LENGTH: 8
<212> TYPE: PRT

```
<213> ORGANISM: Bacillus megaterium

<400> SEQUENCE: 19

Cys Phe Asn Lys Thr Ser Gly Ser
1               5
```

RECOMBINANT VECTOR AND METHOD FOR PRODUCING RECONSTITUTED CYTOCHROME P450 OXYGENASE-REDUCTASE FUSION PROTEIN USING THE SAME

CROSS-REFERENCE TO RELATED APPLICATION AND CLAIM OF PRIORITY

This application claims priority to Korean Patent Applications No. 10-2020-0057020 filed on May 13, 2020 in the Korean Intellectual Property Office (KIPO), the entire disclosure of which is incorporated by reference herein.

BACKGROUND

1. Field of the Invention

The present invention relates to a recombinant vector and a method for producing a reconstituted cytochrome P450 oxygenase-reductase fusion protein using the same.

2. Description of the Related Art

Cytochrome P450 (sometimes abbreviated as "P450," "CYP" and the like for conveying the meaning or relative comparison with existing results in the present disclosure) is a monooxygenase, and is found in most species from archaea, bacteria, fungi, and plants, to animals and humans. In addition, cytochrome P450 is an enzyme involved in the metabolism of steroids, and fatty acids, which are biological components, and fat-soluble vitamins, and the detoxification and excretion of xenobiotics including drugs, carcinogens and pesticides, and has a prosthetic group with a heme structure in which one iron is coordinated to an active site. More than 50,000 cytochrome P450s is described to exist in most forms of life, and thereby, is capable of mediating a wide variety of substrate oxidation type reactions. Thus, cytochrome P450 is a highly valuable enzyme, but is mostly present as a membrane protein, thereby making expression or purification in a foreign host very difficult. In addition, due to the need for an expensive coenzyme (NADPH) for enzyme activity, and the fact that most cytochrome P450s require additional expression of reductase that oxidizes the coenzyme to provide a reducing power, there is a limitation in industrial use of cytochrome P450 (see FIG. 1A).

*Bacillus megaterium*-derived bacterial cytochrome P450 BM3 is expressed in the cytoplasm in a form of single protein containing reductase, thereby it has an advantage that the expression and purification are easily executed compared to other cytochrome P450s in which oxygenase and reductase exist separately (see FIG. 1B). In addition, despite the fact that P450 BM3 is a multi-domain protein having a size of about 119 kDa including two domains of oxygenase and reductase, it has excellent properties capable of being over-expressed to occupy more than 10% of a total protein concentration in *E. coli*, while more than 90% of the expressed protein is expressed in a soluble state. Therefore, P450 BM3 is commonly used as a template for obtaining cytochrome P450 BM3 variants with improved properties such as coenzyme selectivity, substrate specificity and enzyme activity, so as to be suitable for production or toxicity assessment of a compound having a high industrial value through a technique for improving properties of the protein.

However, P450 BM3 over-expressed in *E. coli* has a low expression ratio in a complete form with heme which is a prosthetic group important in enzyme activity, only about 10 to 30% of protein among the total P450 BM3s expressed in *E. coli* has heme required for normal enzyme activity, and it is also known that there is a large deviation in the heme retention. Accordingly, it is difficult to obtain reproducible results because it is difficult to secure a homogenous enzyme. Due to such a problem, despite a high expression level, activity of the enzyme is low, and the deviation in activity between clones is large. In addition, compared to an enzyme produced in an appropriate amount by natural quality control in a cell, an unstable structure without heme produced by artificially forced over-expression in the foreign host also has a low stability. In order to improve such a low heme content, studies such as adjusting culture conditions, changing a composition of a medium such as adding heme precursor to the medium, or increasing the heme concentration in the *E. coli* cytoplasm through a control of metabolic pathway have been performed, but the heme content has not improved significantly. Accordingly, there is an urgent need to deduce a solution for the above-described problems, and when it is possible to homogenously produce cytochrome P450 BM3 having high activity, stability, and reproducibility utilizing the same, it is expected that it may greatly contribute to the construction of a production system for industrial use.

SUMMARY

It is an object of the present invention to provide a recombinant vector which increases a heme content at an active site of oxygenase of a reconstituted cytochrome P450 oxygenase-reductase fusion protein to improve enzymatic activity.

Another object of the present invention is to provide a host cell transformed with the recombinant vector.

In addition, another object of the present invention is to provide a method for producing a reconstituted cytochrome P450 oxygenase-reductase fusion protein by culturing the host cell.

To achieve the above objects, the following technical solutions are adopted in the present invention.

1. A recombinant vector for producing a reconstituted cytochrome P450 oxygenase-reductase fusion protein in which cytochrome P450 oxygenase and reductase for the same are independently expressed and reconstituted, the recombinant vector including: a first polynucleotide which encodes the cytochrome P450 oxygenase; a second polynucleotide which encodes the reductase; and a third polynucleotide which is interposed between the first and second polynucleotides and encodes a split intein.

2. The recombinant vector according to above 1, wherein the first polynucleotide encodes a protein consisting of an amino acid sequence of SEQ ID NO: 1.

3. The recombinant vector according to above 1, wherein the second polynucleotide encodes a protein consisting of an amino acid sequence of SEQ ID NO: 2.

4. The recombinant vector according to above 1, wherein the third polynucleotide encodes a protein consisting of an amino acid sequence of SEQ ID NO: 6.

5. The recombinant vector according to above 1, wherein the first polynucleotide consists of a sequence of SEQ ID NO: 3, the second polynucleotide consists of a sequence of SEQ ID NO: 4, and the third polynucleotide consists of a sequence of SEQ ID NO: 5.

6. A host cell transformed with the recombinant vector according to any one of above 1 to 5.

7. The host cell according to above 6, wherein the host cell is *Escherichia coli*.

8. A method for producing a reconstituted cytochrome P450 oxygenase-reductase fusion protein including: culturing the host cell according to above 6.

9. A reconstituted cytochrome P450 oxygenase-reductase fusion protein having an increased heme content, enzyme activity or stability, which is produced by the method according to above 8.

10. A composition for hydroxylation of a substrate including the reconstituted cytochrome P450 oxygenase-reductase fusion protein according to above 9.

11. The composition according to above 10, wherein the substrate is omeprazole, omeprazole sulfide, ethoxy coumarin or nitrophenol.

The present invention provides a recombinant vector and a method for producing a reconstituted cytochrome P450 oxygenase-reductase fusion protein using the same. According to the present invention, oxygenase and reductase are independently expressed in a host cell into which the recombinant vector is introduced, and then are reconstituted by a split intein, thereby it is possible to increase the heme content contained in the active site of the oxygenase and improve enzyme activity and stability.

BRIEF DESCRIPTION OF THE DRAWINGS

The above and other objects, features and other advantages of the present invention will be more clearly understood from the following detailed description taken in conjunction with the accompanying drawings, in which:

FIG. 1A illustrates eukaryotic-derived cytochrome P450. FIG. 1B illustrates *Bacillus megaterium*-derived cytochrome P450 BM3. FIG. 1C is a schematic diagram illustrating the technical principle of the present invention, which illustrates a comparison between a conventional method for expressing cytochrome P450 BM3 in one protein (P450 BM3 WT portion of FIG. 1C) and the method of the present invention in which two domains of oxygenase and reductase are each independently expressed by fusing a split intein (P450 BM3 IMR portion of FIG. 1C). As can be confirmed in the P450 BM3 IMR portion of FIG. 1C, in the method of the present invention, oxygenase domains containing heme and having a complete structure have higher protein splicing efficiency than the case of without heme, and as a result, reconstituted cytochrome P450 having a high heme content may be produced;

FIG. 2A illustrates two domains of the *Bacillus megaterium*-derived cytochrome P450 protein in which a histidine tag (His tag) is fused to the carboxyl terminus, i.e., reductase domains. Hereinafter, in the present disclosure, the *Bacillus megaterium*-derived cytochrome P450 protein expressed without being split into two domains existing in nature is referred to as "WT" (sometimes referred to as "wild type" in the present disclosure);

FIG. 2B is a schematic diagram illustrating a process of fusing a split intein between two domains of the *Bacillus megaterium*-derived cytochrome P450 protein illustrated in FIG. 2A. Hereinafter, in the present disclosure, the protein reconstituted by split intein using such an expression method is referred to as "intein-mediated reconstituted (IMR) cytochrome P450."

In FIG. 5A, N.C represents a pET24a empty vector, T represents a total protein fraction, and S represents a soluble fraction. Hereinafter, in the drawings illustrating the SDS-PAGE analysis results, T and S have the same meaning as described above.

DETAILED DESCRIPTION

Figure 1A:
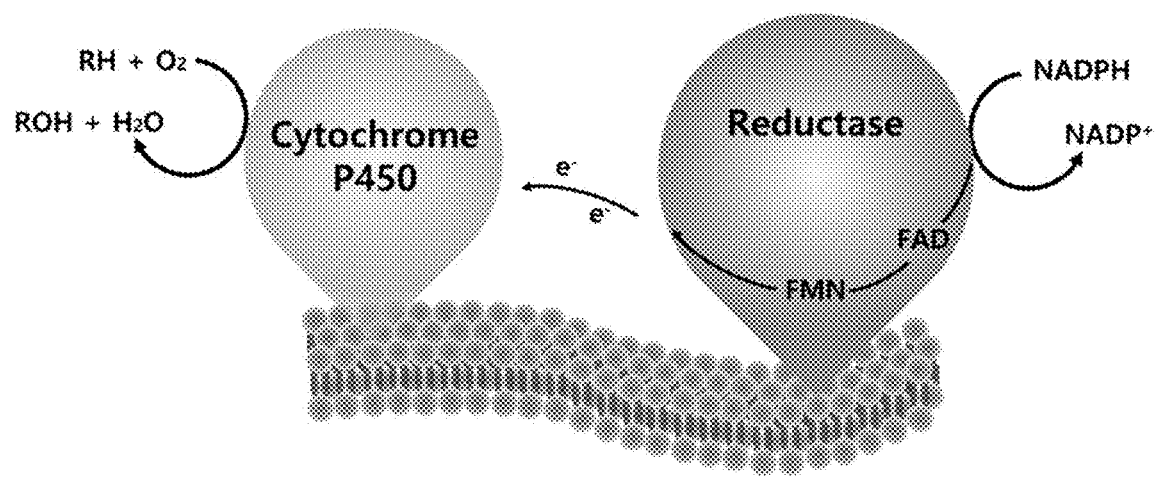
FIGS. 1A to 1C are schematic diagrams illustrating comparisons of technical principles and effects between the present invention and a conventional method.
Figure 1B:
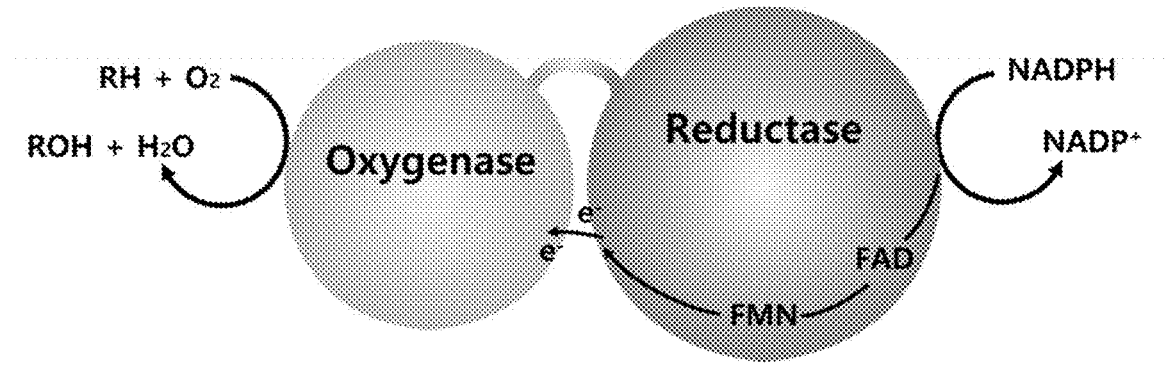
Figure 1C:
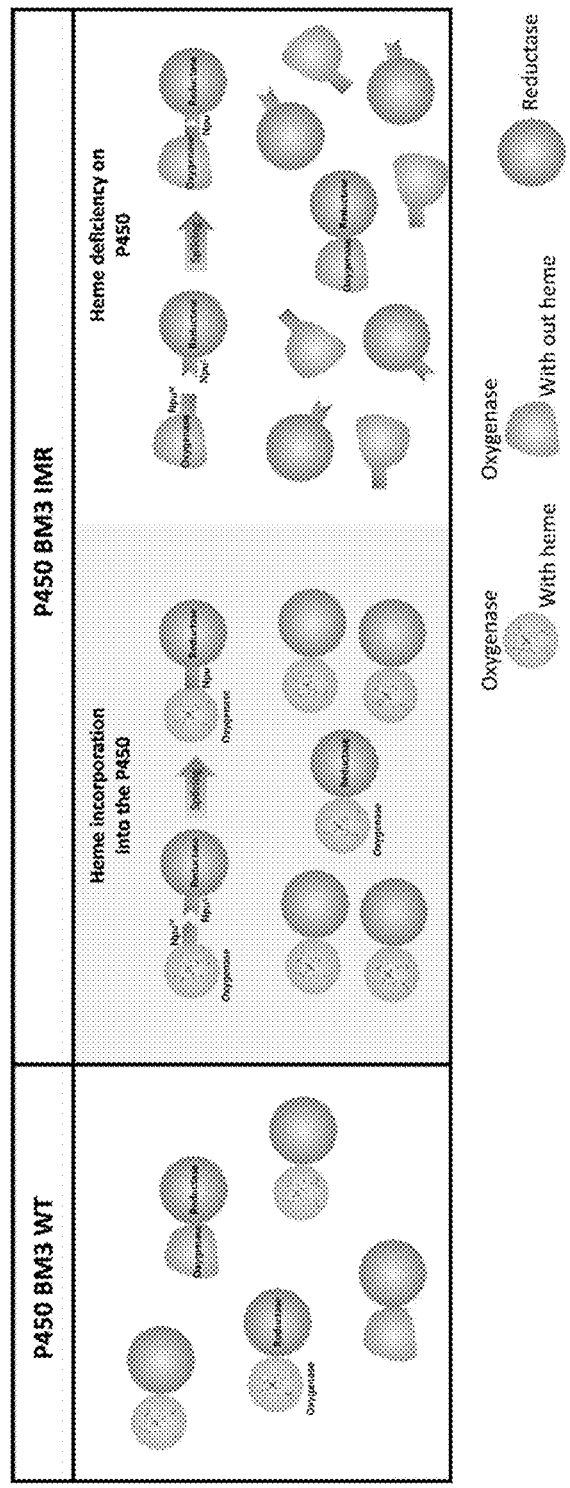

Hereinafter, the present invention will be described in detail.

As used herein, the term "target protein" is a protein to be reconstituted and produced in a form having high activity with secured stability by those skilled in the art, and refers to any protein that can be expressed in a transformant by inserting a polynucleotide encoding the protein into a recombinant expression vector.

The target protein of the present invention may be any one or two or more selected from the group consisting of oxygenase cytochrome P450 (P450 or CYP), (S)-limonene 3-monooxygenase, (S)-limonene 6-monooxygenase, (S)-limonene 7-monooxygenase, 3,9-dihydroxypterocarpan 6a-monooxygenase, 4'-methoxyisoflavone 2'-hydroxylase, 27-hydroxycholesterol 7alpha-monooxygenase, chloride peroxidase, camphor 5-monooxygenase, alkane 1-monooxygenase, cholesterol 7 alpha-monooxygenase, hydroxyphenylacetonitrile 2-monooxygenase, hypotaurine dehydrogenase, indole-3-acetaldehyde oxidase, isoflavone 3'-hydroxylase, linalool 8-monooxygenase, Lucotriene-B4 20-monooxygenase, lignin peroxidase, manganese peroxidase, tryptophan 2'-dioxygenase, spermidine dehydrogenase, steroid 11 beta-monooxygenase, steroid 17alpha-monooxygenase, tryptophan alpha, beta-oxidase, and fragments thereof, but it is not limited thereto.

In addition, as used herein the term "recombinant protein" refers to a protein in which other proteins are linked or other amino acid sequences are added to the amino terminus or carboxyl terminus of the original target protein sequence. In the present invention, the recombinant expression vector is prepared so that proteins which can be fused with two domains forming the cytochrome P450 BM3, i.e., the oxygenase domain and the reductase domain to induce reconstitution of each folded domain and expressed between the two domains, for example, split inteins are simultaneously expressed. Then, the oxygenase domain and the reductase domain expressed by the recombinant expression vector are reconstituted into a complete cytochrome P450 BM3 protein by a protein splicing reaction of split intein.

In addition, the terms "vector," "expression vector," or "recombinant expression vector" is a linear or circular DNA molecule that includes an element and an additional fragment provided for gene transcription and translation, and encodes polynucleotide operably linked thereto. The additional fragment includes a promoter, a transcription termination sequence and the like. The vector, expression vector, or recombinant expression vector includes one or more replication origins, one or more selection markers and the like. The vector, expression vector, or recombinant expression vector is generally derived from plasmid or viral DNA, or contains both elements.

The present invention provides a recombinant vector which is a recombinant vector for producing a cytochrome P450 oxygenase-reductase fusion protein in which cytochrome P450 oxygenase and reductase for the same are independently expressed and reconstituted, the recombinant vector includes: a first polynucleotide which encodes the cytochrome P450 oxygenase; a second polynucleotide which encodes the reductase; and a third polynucleotide which is interposed between the first and second polynucleotides and encodes a split intein.

The recombinant vector of the present invention is intended to be reconstituted into one protein in which the cytochrome P450 oxygenase and the reductase for the same are independently expressed, and then the oxygenase and the reductase are linked with each other by spontaneous protein splicing of the split intein.

Oxygenase of the cytochrome P450 is not particularly limited in terms of its origin, but may be, for example, derived from bacteria, and specifically may consist of an amino acid sequence of SEQ ID NO: 1 derived from *Bacillus megaterium*.

The first polynucleotide is not limited so long as it encodes the cytochrome P450 oxygenase, and may encode, for example, a protein consisting of the amino acid sequence of SEQ ID NO: 1.

The first polynucleotide may consist of a sequence of SEQ ID NO: 3.

The reductase is not particularly limited in terms of its origin so long as it oxidizes coenzymes to provide a reducing power to the cytochrome P450 oxygenase, for example, may be derived from bacteria, and specifically may consist of an amino acid sequence of SEQ ID NO: 2 derived from *Bacillus megaterium*.

The oxygenase and reductase may be derived from different species each other. In this case, known sequences of each species may be used.

The second polynucleotide is not limited so long as it encodes the reductase for the cytochrome P450 oxygenase, and may encode, for example, a protein consisting of the amino acid sequence of SEQ ID NO: 2.

The second polynucleotide may consist of a sequence of SEQ ID NO: 4.

The split intein is interposed between the first and second polynucleotides.

The split intein has spontaneous peptide cleavage and ligation abilities, and the split intein used herein may vary according to types of the target protein, for example, the split intein may be derived from *Nostoc punctiforme*.

In addition, the split intein may be configured so that an extein sequence is further fused to the terminus as necessary. For example, the extein may consist of an amino acid sequence such as a wild type "CFNKTSGS" (SEQ ID NO: 19), but it is not limited thereto, and if necessary, mutation may be introduced therein through deletion of some amino acids from the amino acid sequence, addition of other amino acids, substitution to other amino acids or the like.

The third polynucleotide is not particularly limited so long as it encodes the split intein, and may include, for example, a polynucleotide encoding a DnaE protein derived from *Nostoc punctiforme* consisting of a sequence of SEQ ID NO: 5.

The first polynucleotide, the third polynucleotide and the second polynucleotide may be sequentially linked. Specifically, a 5' end of the third polynucleotide may be fused to a 3' end of the first polynucleotide, and a 3' end of the third polynucleotide may be fused to a 5' end of the second polynucleotide. In this case, for example, the first polynucleotide may consist of the sequence of SEQ ID NO: 3, the second polynucleotide may consist of the sequence of SEQ ID NO: 4, and the third polynucleotide may consist of the sequence of SEQ ID NO: 5.

The first polynucleotide, the second polynucleotide and the third polynucleotide are operably linked to a promoter.

As used herein, the term "operably linked" means a state in which a sequence for control of nucleic acid expression and the target protein or a nucleic acid sequence encoding RNA are functionally linked so as to perform a general function. For example, the promoter and the protein or the nucleic acid sequence encoding RNA may be operably linked to affect the expression of the encoding sequence. Operable linkage with the expression vector may be made using genetic recombination techniques well known in the art, and site-specific DNA cleavage and linkage may be performed using enzymes and the like generally known in the art.

The promoter may be derived from a target intended to introduce the recombinant vector of the present invention, and types thereof are not limited. For example, it may be a T7 promoter.

In the host cell into which the recombinant vector is introduced, the first polynucleotide and the second polynucleotide may be independently expressed, and these polynucleotides may be reconstituted into one target protein through protein splicing of split inteins encoded by the third polynucleotide.

The recombinant vector of the present invention may use a plasmid vector, a cosmid vector, a bacteriophage vector, a viral vector, and the like as a template, but it is not limited thereto. Suitable recombinant vectors may include expression control elements such as a promoter, operator, initiation codon, termination codon, polyadenylation signal, enhancer, and the like, and may be variously prepared according to the purposes.

The recombinant vector may include an antibiotic resistance marker for screening the host into which the vector is introduced, which may be either inherent in the vector or introduced externally.

The present invention provides a host cell transformed with the recombinant vector.

The host cell may be used to express oxygenase of P450, split intein and reductase of P450, and reconstitute the oxygenase and reductase into one protein by introducing the recombinant vector of the present invention therein.

The host cell is not particularly limited, and may be, for example, strains of genus *Escherichia*, genus *Salmonella*, genus *Shigella*, genus *Enterobacter*, genus *Proteus*, genus *Pseudomonas*, genus *Moraxella*, genus *Helicobacter*, genus *Stenotrophomonas*, genus *Bdellovibrio*, genus *Legionella*, genus *Neisseria*, and *Erwinia*, etc., and specifically, *Escherichia coli*. More specifically, the host cell may be *E. coli* BL21 (DE3).

The transformation may be performed by conventional methods known in the art, and may be introduced, for example, through a natural introduction method, thermal shock method, electric shock method, or the like, but it is not particularly limited thereto.

The present invention provides a method for producing a reconstituted cytochrome P450 oxygenase-reductase fusion protein including the step of culturing the host cell.

The host cell is as described above.

Conditions for culturing the host cell are not particularly limited, and known culture conditions may be used.

As a microbial culture medium, mediums known in the art may be used, and for example, a Luria-Bertani (LB) medium may be used, but it is not limited thereto.

When the host cell expresses a reconstituted target protein by introducing the recombinant vector, the culture medium may further include an antibiotic for screening transformed microorganisms.

If necessary, the culture medium may further include IPTG to promote expression of the reconstituted target protein.

In the above-described method, the reconstituted target protein may be obtained by separating it from the culture of the host cell.

The culture may be a host cell or a culture medium thereof.

The host cell may be disrupted for easier separation of the reconstituted cytochrome P450 fusion protein.

The host cell may be physically disrupted by ultrasonication etc., or chemically disrupted by a surfactant, etc., but it is not limited thereto.

The culture medium may be a medium containing the host cell, or a medium from which the host cell is separated.

In addition, the production method of the present invention may further include the step of separating and purifying the reconstituted cytochrome P450 oxygenase-reductase fusion protein. The above step may be performed in connection with a conventional process in the art performed to use the produced protein for an intended use.

The reconstituted cytochrome P450 oxygenase-reductase fusion protein prepared by the above-described method may have an increased heme content, enzyme activity or stability.

The present invention provides a composition for hydroxylation of a substrate including the reconstituted cytochrome P450 oxygenase-reductase fusion protein.

The substrate may be omeprazole, omeprazole sulfide, ethoxycoumarin, nitrophenol and the like.

The composition includes the reconstituted cytochrome P450 oxygenase-reductase fusion protein having the increased enzyme activity, and thus may be used as an enzyme catalyst for a hydroxylation reaction of a wide range of substrates.

Hereinafter, the present invention will be described in detail with reference to examples.

Experimental Material

Reagents, materials and protocols used for polymerase chain reaction (PCR) amplification, DNA cloning, transformation, and the like in the present example are as follows, which will be apparent to those skilled in the art.

*E. coli* XL1-Blue was purchased from Stratagene (USA) and used.

*E. coli* BL21 (DE3) was purchased from Stratagene (USA) and used.

pET24a plasmid was purchased from New England Labs (UK) and used.

Primers for amplification of pET24a-oxygenase-reductase (pET24a-WT) were synthesized by BIONICS (Korea) and used.

pGEM-Npu_PCC73102 plasmids were synthesized by Bioneer (Korea) and used.

nPfu-Special DNA polymerase was purchased from Enzynomics (Korea) and used.

In-Fusion® HD cloning kit was purchased from Takara Korea Biomedical Inc. (Korea) and used.

Other XbaI and EcoRI restriction enzymes were purchased from New England Biolabs (UK) and used.

Other reagents were purchased from Sigma Aldrich (USA), etc. and used.

*E. coli* XL1-Blue was used as a host for plasmid transformation and genetic manipulation, and *E. coli* BL21 (DE3) was used for protein production.

In order to induce spontaneous splicing of intein, since asparagine is preferred as the first amino acid of N terminus-intein and the last amino acid of carboxyl-intein, and cysteine is preferred as amino acid linked to the last amino acid of carboxyl terminus intein, primers for PCR were prepared in consideration of the above fact.

EXAMPLE

[Example 1] Preparation of Recombinant Gene for Reconstitution of Oxygenase and Reductase Domains of Bacterial Cytochrome P450 BM3 Using Protein Splicing Handling of DNA used in preparation of plasmids required for the present invention was performed based on the standard protocol.

Independent expression of the oxygenase domain and reductase domain forming *Bacillus megaterium*-derived cytochrome P450 BM3 and fusion of split intein for post-translational reconstitution of the two domains were performed through a PCR reaction. Respective primers including the following sequences were synthesized and used for this PCR reaction. The primers used in the experiment are shown in Table 1 below.

Figure 4:
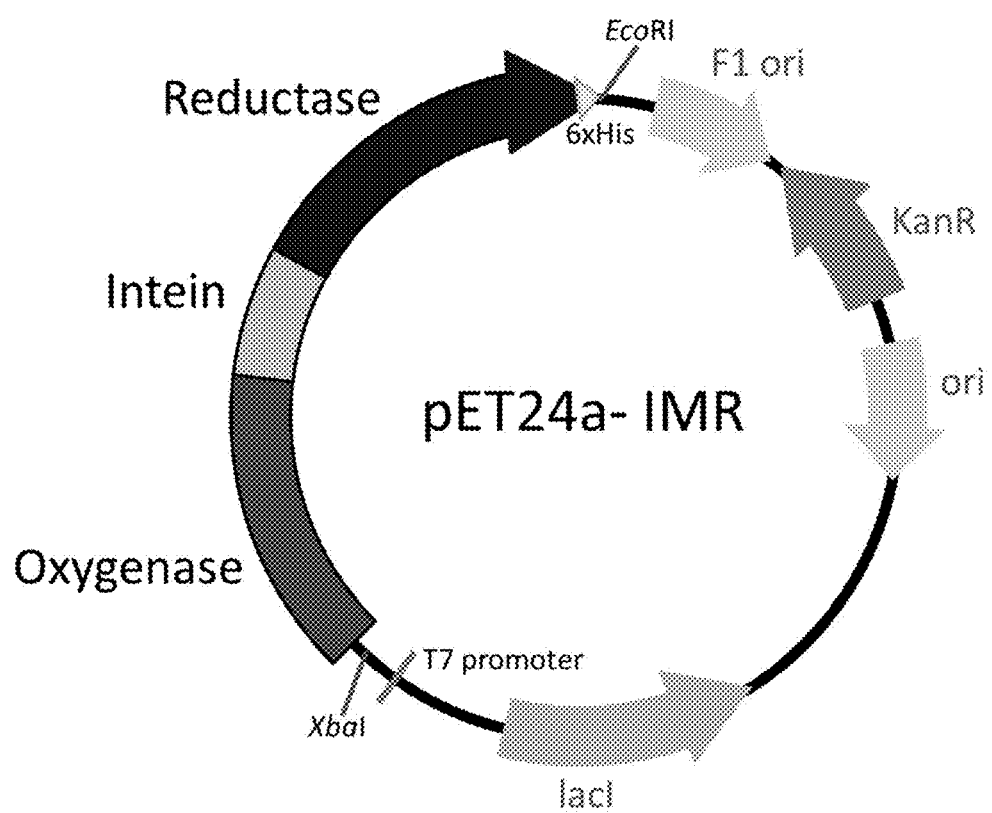
FIG. 4 is a diagram illustrating recombinant expression vector pET24a-IMR (oxygenase-intein-reductase)

The oxygenase-split intein-reductase structure, which is prepared so that the amino terminus region of the split intein is fused to the carboxyl terminus of the oxygenase domain illustrated in FIG. 4 and the carboxyl terminus region of the split intein is fused to the amino terminus of the reductase domain, was designed so as to be able to remove the oxygenase domain by XbaI and NheI and the reductase domain by SpeI and EcoRI. Therefore, the oxygenase or

TABLE 1

| Primer name | Sequence (5' → 3') | Restriction enzyme |
|---|---|---|
| BM3_#10 F | 5'- GGA GAT ATA CATATG ACA ATT AAA GAA ATG CCT CAG CC -3' (SEQ ID NO: 9) | XhoI |
| BM3_#10 R | 5'- ACG GAG CTC GAATTC TTA GTG ATG GTG ATG GTG ATG CCC AGC CCA CAC GTC-3' (SEQ ID NO: 10) | EboRI |
| OXI INFUSION F | 5'- TAA CAA TTC CCC TCT AGA AAT AAT TTT GTT TAA CTT TAA GAA GGA GAT ATA CATATG AC -3' (SEQ ID NO: 11) | XhoI |
| OXI OVERLAP R | 5'- GTA CAG CTA GCC TGT TCA GTG CTA GGT GAA G - 3' (SEQ ID NO: 12) | |
| RE OVERLAP F | 5'- CAA GAC TAG TTC TGC TAA AAA AGT ACG CAA AAA GGC -3' (SEQ ID NO: 13) | |
| RE INFUSION R | 5'- TCG ACG GAG CTC GAATTC TTA GTG ATG GTG ATG GTG ATG CCC AG - 3' (SEQ ID NO: 14) | EboRI |
| INTEIN OVERLAP F | 5'- CAC TGA ACA GGC TAG CTG TAC TAA ATG TCT GAG CTA TGA AAC C -3' (SEQ ID NO: 15) | |
| INTEIN INFUSION R | 5'- GCG TAC TTT TTT AGC AGA ACT AGT CTT GTT AAA GCA GTT GCT TGC -3' (SEQ ID NO: 16) | |

Polynucleotide encoding *Bacillus megaterium*-derived cytochrome P450 BM3 protein (WT) was amplified by PCR using pET24a-WT provided from Chonnam National University as templates and primers of SEQ ID NOs: 9 and 10 (see FIG. 2A), a first polynucleotide encoding the oxygenase domain of *Bacillus megaterium*-derived P450 BM3 protein, and a second polynucleotide encoding the reductase domain were amplified in a form capable of overlapping PCR with the split intein, using the product obtained through the above process as templates and the primers of SEQ ID NOs: 11 and 12, and SEQ ID NOs: 13 and 14. In addition, a third polynucleotide encoding a split intein for inducing protein splicing was amplified in a form capable of overlapping PCR an amino terminus region of the split intein with the oxygenase domain and the carboxyl terminus with the reductase domain, using plasmid pGEM-Npu_PCC73102 as a template and primers of SEQ ID NOs: 15 and 16. Based on the PCR product obtained as described above, the overlapping PCR was performed as illustrated in FIG. 2B. In all the PCR reactions, nPfu-Special DNA polymerase with a low frequency in mutation was used.

Figure 2A:
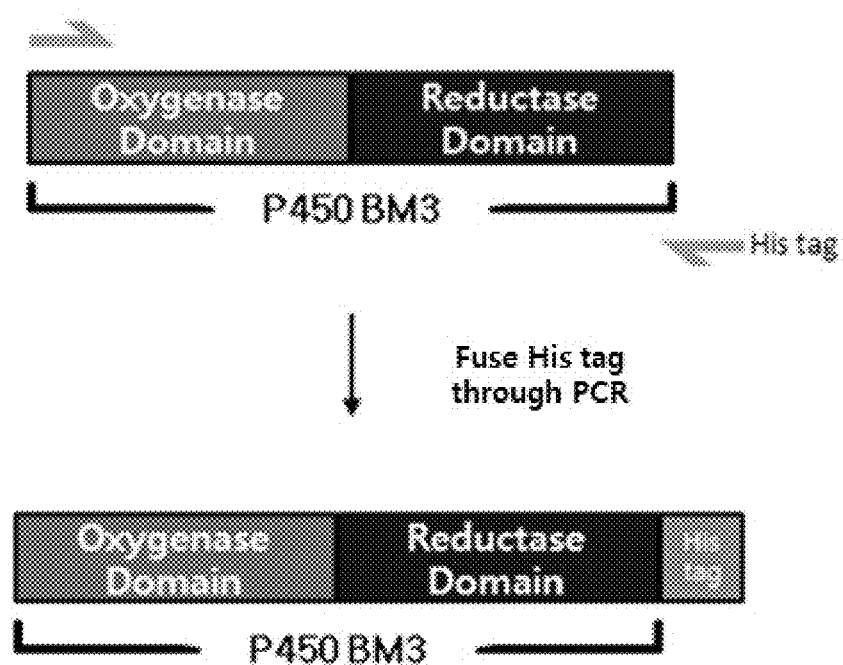
FIGS. 2A and 2B are schematic diagrams of a target gene to be inserted into an expression vector.
Figure 2B:
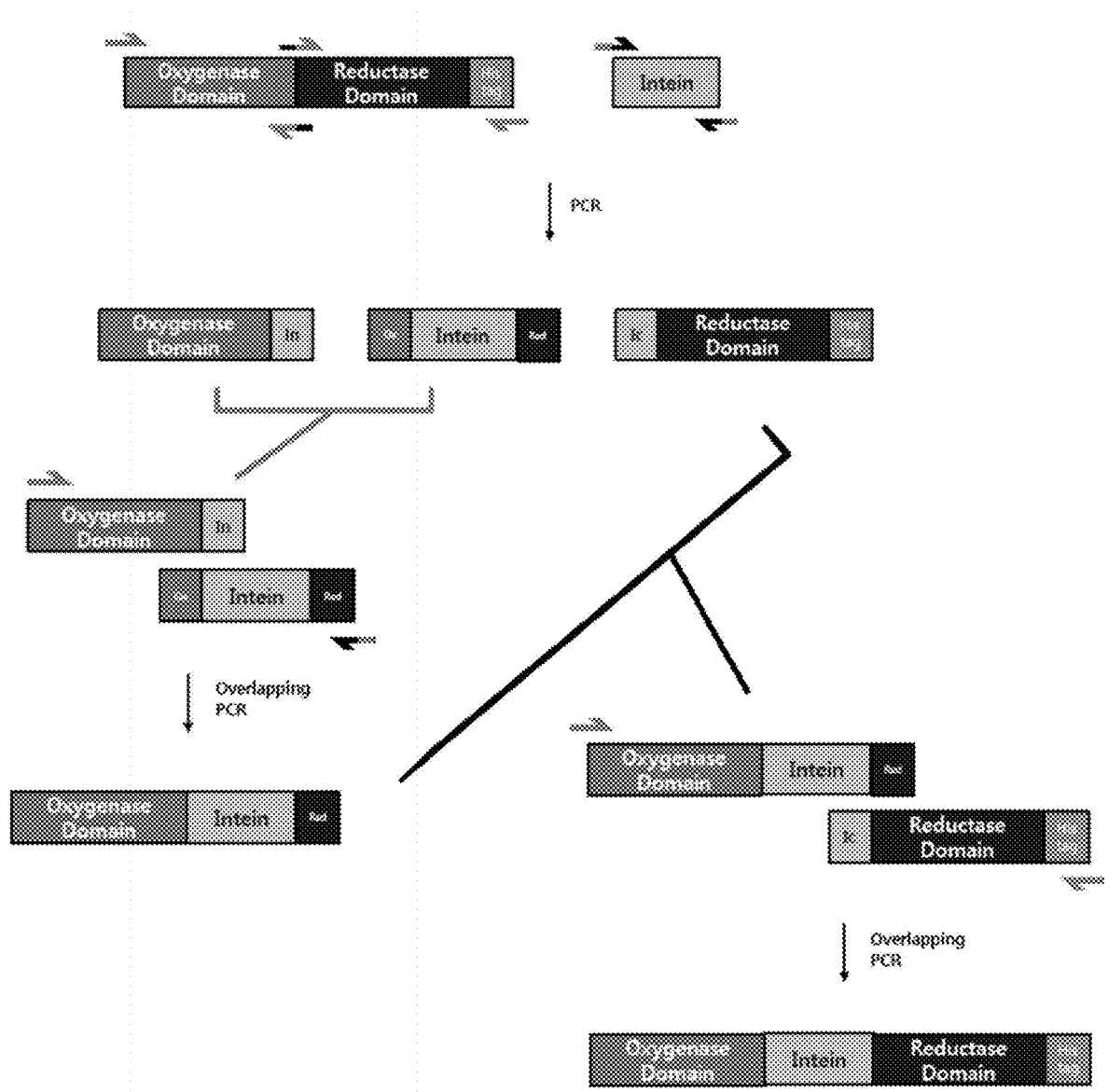
Figure 3:
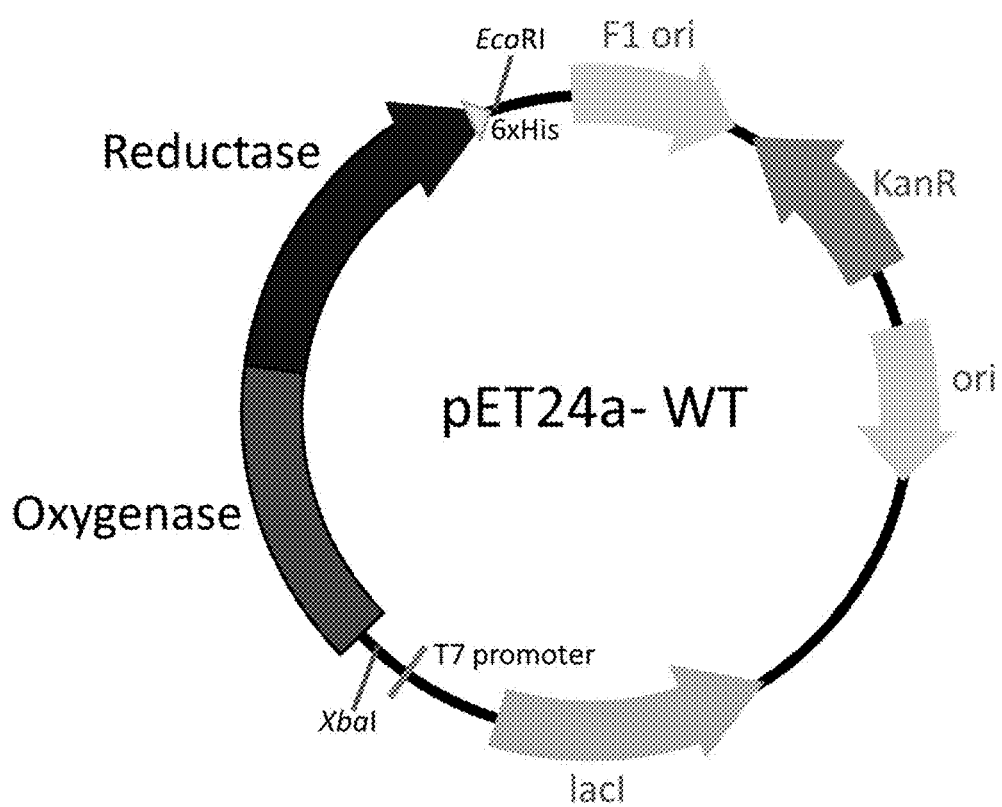
FIG. 3 is a diagram illustrating recombinant expression vector pET24a-WT (oxygenase-reductase)

The DNA fragments obtained through PCR respectively illustrated in FIGS. 2A and 2B were cloned by an In-Fusion® HD cloning kit into pET24a plasmid treated with XbaI and EcoRI restriction enzymes, respectively, such that the recombinant expression vector, pET24a-oxygenase-reductase (pET24a-WT) as illustrated in FIG. 3 and the recombinant expression vector, pET24a-oxygenase-split intein-reductase (pET24a-IMR) as illustrated in FIG. 4 were prepared.

reductase domain derived from any cytochrome P450 (including a protein in eukaryote including BM3) was cloned so as to be able to form hybrid cytochrome P450 including oxygenase and reductase derived from different species of cytochrome P450.

[Example 2] Confirmation of Reconstitution of Oxygenase and Reductase Domains Independently Expressed Through Split Intein After two domains of cytochrome P450 BM3 were fused with split intein and independently expressed, in order to confirm whether these domains were functionally reconstituted by a protein splicing reaction of the split intein, expression patterns were compared with wild type cytochrome P450 BM3. Subsequently, pET24a-oxygenase-reductase in which the wild type cytochrome P450 BM3 gene prepared in Example 1 is cloned and pET24a-oxygenase-split intein-reductase in which the two domains are fused with the split intein and independently expressed were respectively transformed into *E. coli* XL1-Blue according to methods apparent to those skilled in the art, and then spread on a Luria-Bertani (LB) solid medium containing 50 μg/mL of kanamycin, followed by culturing overnight at 37° C. Then, *E. coli* XL1-Blue into which the recombinant expression vector is introduced were inoculated in an LB liquid medium containing 50 μg/mL of kanamycin, respectively, followed by shaking culture at 200 rpm and 37° C. to purely separate the recombinant expression vector by a purification kit (Promega) using the cultured cells. The recombinant expression vectors obtained through the above process were then transformed into *E. coli* BL21 (DE3), respectively, and then spread on the LB solid medium containing 50 µg/mL kanamycin, followed by culturing overnight at 37° C. A single clone grown in the medium was inoculated in an LB liquid medium containing 50 µg/mL kanamycin, and then absorbance was measured while pre-incubating at 200 rpm and 37° C. When the absorbance (600 nm) of the culture medium reached 2.0 to 2.5, the recombinant expression vectors were passaged in an LB liquid medium having the same composition as above, followed by culturing at 600 nm until the absorbance reached 0.6 to 0.8. Thereafter, 100 mM IPTG was added thereto so that a final concentration would be 0.2 mM, and further cultured for 2.5 hours under the same condition as above.

After completion of the incubation, cells were harvested by correcting so that the absorbance at 600 nm would be 2.0. After resuspending the cells in 300 µl of 20 mM Tris-HCl (pH 8.0), the cells were disrupted by ultra-sonication. Immediately after disruption, total protein fractions were taken, followed by centrifugation at 16,000×g for 30 minutes at 4° C. to remove insoluble aggregates, then soluble fractions were sorted.

5× sample loading buffers (0.225 M Tris-HCl pH 6.8, 50% glycerol, 5% SDS, 0.005 M bromophenol blue and 0.25 M dithiothreitol (DTT)) were added to the samples taken at each step in a ratio of 5:1, and heated for 15 minutes at 100° C. to induce denaturation of all proteins. Subsequently, after slowly cooling each sample, the prepared samples were loaded on 8% acrylamide gel and fixed thereto at 160 V, followed by performing electrophoresis. After the electrophoresis was completed, the acrylamide gel was stained with a Coomassie Brilliant Blue staining solution, and the expression patterns of oxygenase-reductase (WT) and IMR in which the oxygenase domain and the reductase domain are independently expressed with split intein were compared and analyzed.

Figure 5A:
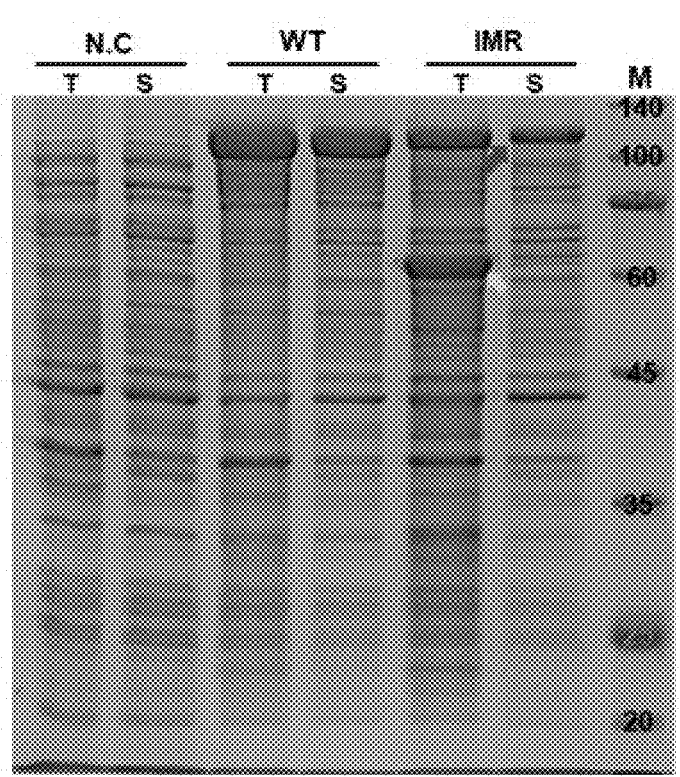
FIG. 5A is an image illustrating SDS-PAGE analysis results that can confirm an expression pattern of the *Bacillus megaterium*-derived P450 protein expressed under the control of T7 promoter.

FIG. 5A illustrates SDS-PAGE analysis results for the above-mentioned two proteins. As can be confirmed in FIG. 5A, in the case of the wild type protein, bacterial cytochrome P450 BM3, an over-expressed protein band can be observed at about 119 kDa position similar to known in the art. When expressing IMR, the oxygenase and reductase domains were shown at about 63 kDa and 69 kDa, which are theoretical sizes associated with the split intein, respectively, and over-expressed bands can be observed at 119 kDa position which is presumed to be reconstituted by protein splicing of the two domains. Therefore, it can be seen that the product reconstituted by the split intein as well as each domain are the same as the wild type cytochrome P450 BM3 in terms of the size.

In the above process, a form in which two genes are expressed in one promoter, i.e., polycistronic mRNA was configured by inserting a ribosome binding site between the amino and carboxyl terminus regions of the intein, so that the oxygenase and the reductase domains of the cytochrome P450 BM3 could be expressed spatially adjacent to each other upon independent expression thereof. In this case, it is a general phenomenon that an expression level of the gene close to the promoter is higher than that of the gene far away from the promoter, and also in the case of cytochrome P450 BM3, the expression level of the oxygenase close to the promoter is higher than that of the reductase. In the case of the bacterial cytochrome P450 BM3, it is expected that two proteins (oxygenase and reductase) will be fused into one protein during an evolution process, and it is known that independent expression of each domain is also well executed. Therefore, despite the fact that there will be no significant difference in the expression or stability of the two domains, it is expected that the reason, in which intracellular expression level of the reductase domain is about more than 10 times lower than that of oxygenase, is related to a structural deformation generated by fusion with the split intein.

Figure 5B:
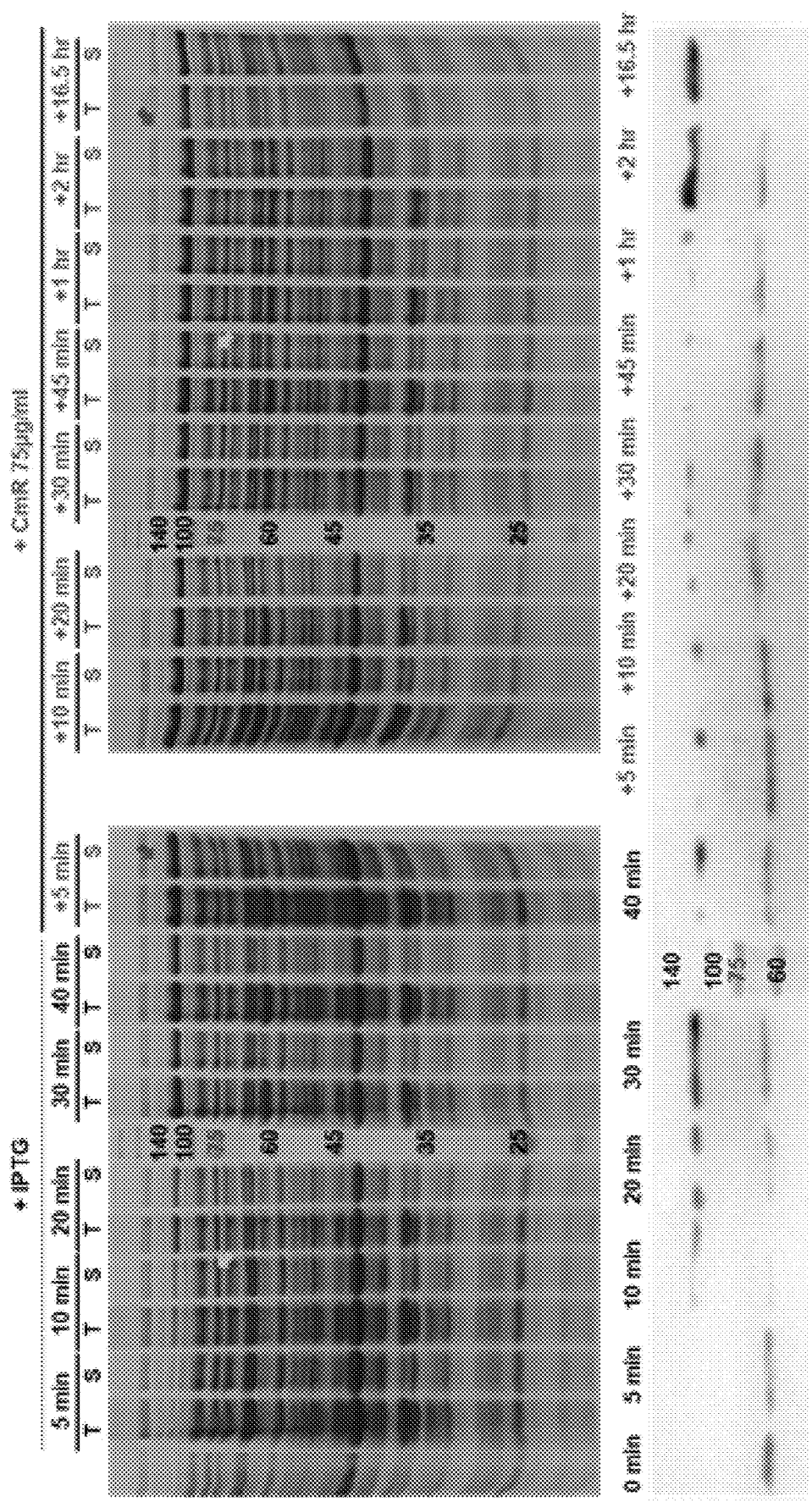
FIG. 5B is images illustrating SDS-PAGE analysis results and western blotting analysis results that can confirm results obtained by adding isopropyl-1-thio-β-D-galactopyranoside (IPTG) under the control of the T7 promoter and inducing protein expression for 40 minutes, followed by treating the same with 75 μg/mL of chloramphenicol to inhibit further a protein synthesis in-vivo, then splicing the P450 protein.

To more accurately observe reconstitution efficiency of bacterial cytochrome P450 BM3 through protein splicing by intein, an amount of cytochrome P450 BM3 reconstituted after the induction of expression was confirmed over time. The experimental process was performed in the same manner as the process for deriving the SDS-PAGE analysis results of FIG. 5A, but after adding IPTG and further incubating for 40 minutes, chloramphenicol antibiotic, which inhibits further protein synthesis in-vivo through a mechanism that suppresses peptidyl transferase activity by binding to 50S subunit of ribosome, was treated at a concentration of 75 µg/mL, thus to suppress additional protein synthesis. Therefore, after the treatment with chloramphenicol, only the already expressed oxygenase-intein amino terminus and intein carboxyl terminus-reductase become components for reconstitution of cytochrome P450 BM3 through protein splicing. Results obtained by measuring the reconstitute efficiency over time by SDS-PAGE and western blotting utilizing an antibody that recognizes a histidine tag (6×His) fused to the reductase domain carboxyl terminus are shown in FIG. 5B. As can be seen from the western blotting results of FIG. 5B, it can be confirmed that the reconstituted cytochrome P450 BM3 is generated after 10 minutes have elapsed from the induction of expression by addition of IPTG. In addition, from the fact that the amount of reconstituted cytochrome P450 is increased after the treatment with chloramphenicol to inhibit protein synthesis, it can be seen that the cytochrome P450 BM3 is reconstituted through protein splicing of oxygenase and reductase domains, which are independently expressed through the split intein.

As described above, in the present invention, it could be confirmed that the recombinant expression vector system prepared to induce reconstitution of the oxygenase domain and the reductase domain through protein splicing by the split intein was normally operated.

Verification of Base Sequence

Under the above conditions, conventional sequencing was performed on the recombinant expression vector used for the expression of two P450 wild type and IMR proteins. As a result, all of the analyzed base sequences were identical to the base sequence of the recombinant expression vector for expression of the P450 protein prepared in the present invention (SEQ ID NO: 18).

[Example 3] Purification of Bacterial Cytochrome P450 BM3 Wild Type and IMR

Cell culture for purification of cytochrome P450 BM3 wild type and IMR was performed by increasing the culture volume to 150 mL according to the same procedure as in Example 2.

Each harvested cell was resuspended by adding 40 mL of phosphate-buffered saline (PBS) containing 20 mM of imidazole. Subsequently, the resuspended cells were disrupted by ultra-sonication, and centrifuged at 16,100×g for 1 hour at 4° C. to separate a supernatant from which insoluble aggregates were removed. Thereafter, 80 mL of PBS containing 20 mM of imidazole was added thereto, respectively, and 120 mL of soluble protein solutions containing wild type or IMR were loaded into a 5 mL of HisTrap column (GE healthcare Life Science, US), respectively. After loading of each soluble protein fraction was completed, the HisTrap column was sufficiently washed with PBS in an amount of 10 times or more of the column volume, and by using PBS containing 160 mM of imidazole, elution of wild type and IMR proteins was performed by inducing a concentration gradient of imidazole.

Figure 6A:
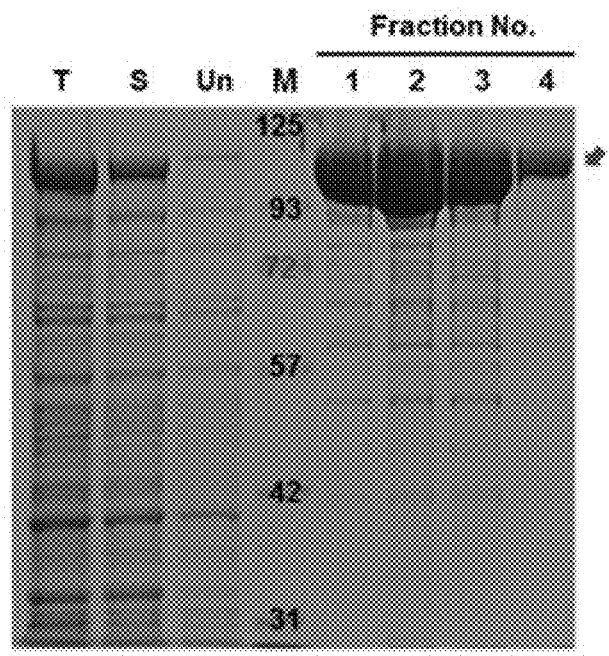
FIGS. 6A and 6B are images respectively illustrating SDS-PAGE analysis results that can confirm results obtained by purifying the *Bacillus megaterium*-derived P450 protein expressed using the recombinant expression vector (pET24a-WT) of FIG. 3 and the recombinant expression vector (pET24a-IMR) of FIG. 4, i.e., the WT of FIG. 5A and the IMR of FIG. 5B by using the histidine tag.
Figure 6B:
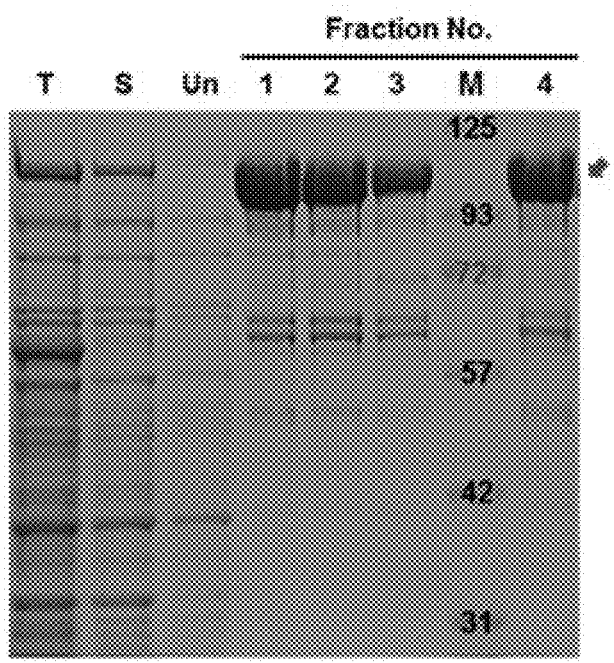

The SDS-PAGE analysis results of fractions collected after the elution of cytochrome P450 BM3 wild type and IMR proteins are illustrated in FIGS. 6A and 6B. As can be confirmed in FIGS. 6A and 6B, 5 mg or more of cytochrome P450 BM3 wild type and IMR proteins were purified in a single process with a high purity of about 90 to 95% or more.

[Example 4] Comparison of Heme Content of Bacterial Cytochrome P450 BM3 Wild Type and IMR Heme contents of the purified cytochrome P450 BM3 wild type and IMR were measured according to the method described in the document [see Guengerich, F. P., Martin, M. V., Sohl, C. D., & Cheng, Q. (2009). Measurement of cytochrome P450 and NADPH-cytochrome P450 reductase. Nature protocols, 4(9), 1245], and results thereof are illustrated in FIG. 7.

Figure 7:
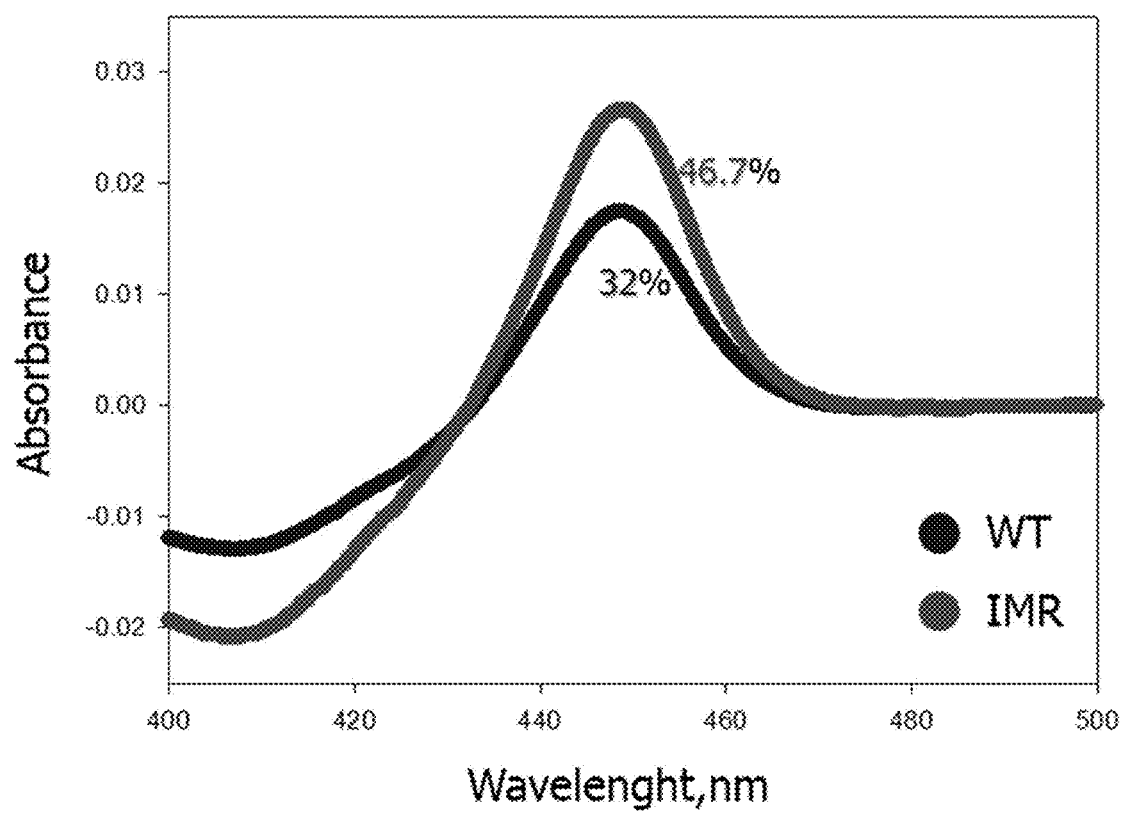
FIG. 7 is a graph illustrating results obtained by analyzing and comparing a difference in CO spectra measured using two P450 proteins respectively purified from FIGS. 6A and 6B, i.e., the WT and IMR.

As can be seen in FIG. 7, it was confirmed by measurement that in the case of wild type cytochrome P450 BM3, only 32% of the entire protein used for the measurement has heme, whereas in the case of reconstituted cytochrome P450 BM3 IMR after independent expression of two domains oxygenase and reductase through the split intein, 47% of the measured entire protein has heme. As can be seen from the above results, in the case of the reconstituted cytochrome P450 BM3 IMR prepared through the protein splicing process after the independent expression of the two domains using the split intein, about 50% of heme is increased as compared to the case in which the above process is not performed (in the case of WT). This is a significant increase that can directly affect activity of P450 protein.

[Example 5] Comparison of Enzyme Activity Between Bacterial Cytochrome P450 BM3 Wild Type and IMR In order to confirm the effect of high heme content on the enzyme activity, the activities of various substrates were compared. Cytochrome P450 BM3 has been reported to be active against various xenobiotics, and is used as a model system for drug safety verification based on this report. In addition, the model system is also commonly utilized in a hydroxylation process of high-value products for increasing physiological activity of the cytochrome P450 BM3. Based on the hydroxylation activity of this cytochrome P450 BM3, activities of cytochrome P450 BM3 wild type (WT) and IMR for various substrates, for example omeprazole, 7-ethoxycoumarin, and p-nitrophenol were compared. First, measurement of enzyme activity of cytochrome P450 BM3 wild type (WT) and IMR for omeprazole was performed according to the procedure described in the document [see Ryu, S. H., Park, B. Y., Kim, S. Y., Park, S. H., Jung, H. J., Park, M., Yun, C. H. (2014). Regioselective hydroxylation of omeprazole enantiomers by bacterial CYP102A1 mutants. Drug Metabolism and Disposition, 42(9), 1493-1497.], which was based on the heme contents obtained through spectrum measurement of a difference in CO. The measurement results are illustrated in FIG. 8.

Figure 8:
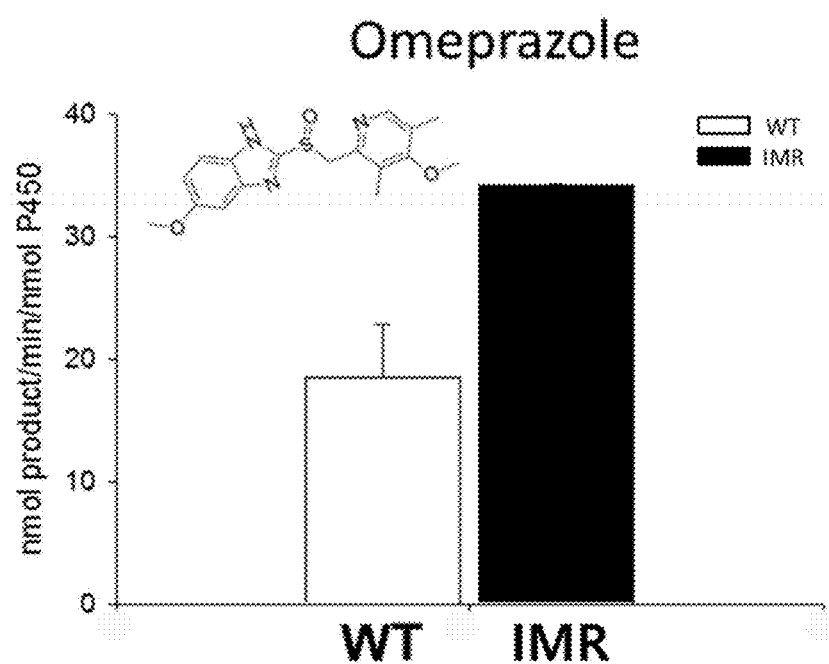
FIG. 8 is a graph illustrating results obtained by measuring and comparing the enzyme activity of two P450 proteins, i.e., the WT and IMR, which hydroxylate a substrate omeprazole based on the results measured in FIG. 7.

As can be seen in FIG. 8, it can be confirmed that, in the case of the cytochrome P450 BM3 IMR in which reconstitution of the oxygenase domain and reductase domain due to the protein splicing process by fusing the split intein is induced, the activity of the enzyme that hydroxylates omeprazole is increased by about 2 times as compared to the wild type.

Figure 9A:
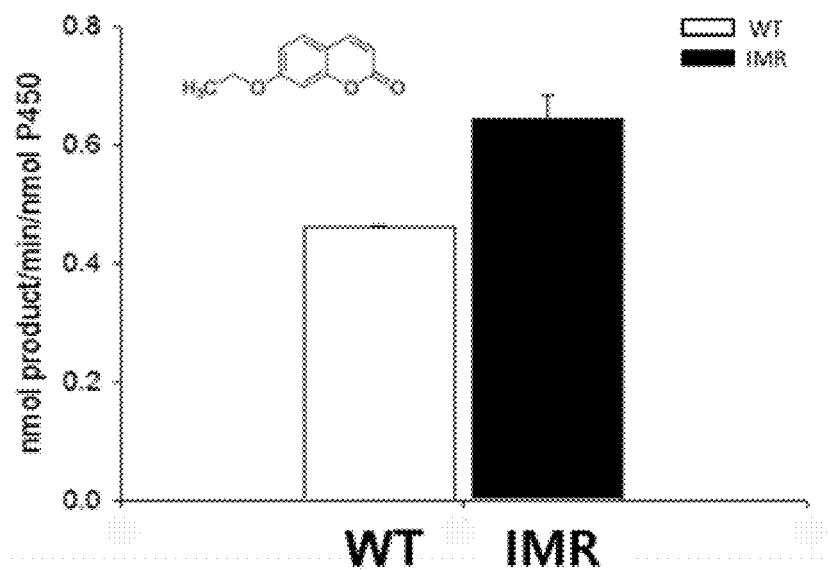
FIG. 9A is a graph illustrating results obtained by measuring and comparing enzyme reaction results in which each of two P450 proteins, i.e., the WT and IMR hydroxylates 7-ethoxycoumarin as a substrate to generate 7-OH coumarin.
Figure 9B:
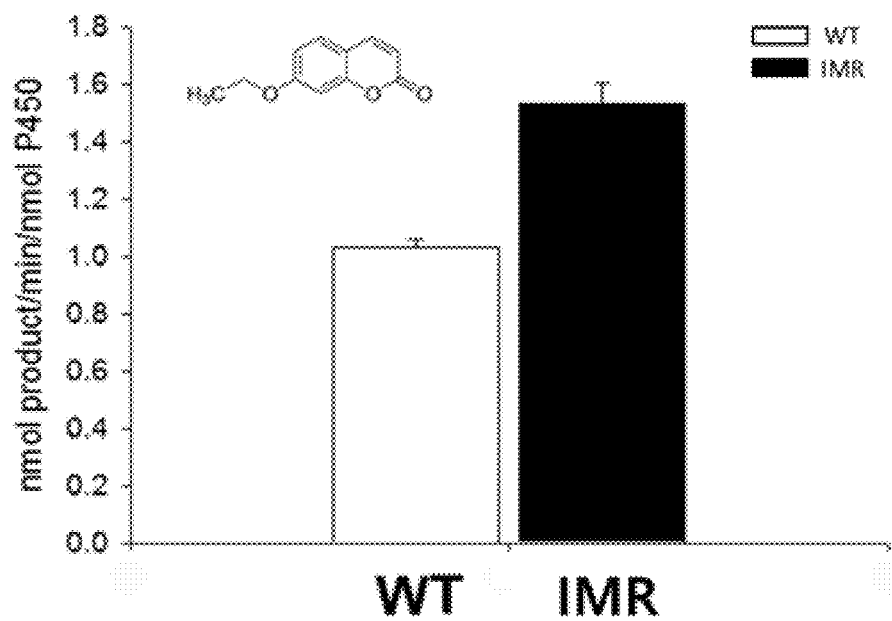
FIG. 9B is a graph illustrating results obtained by measuring and comparing enzyme reaction results in which each of two P450 proteins, i.e., the WT and IMR hydroxylates 7-ethoxycoumarin as a substrate to generate 3-OH 7-coumarin.
Figure 9C:
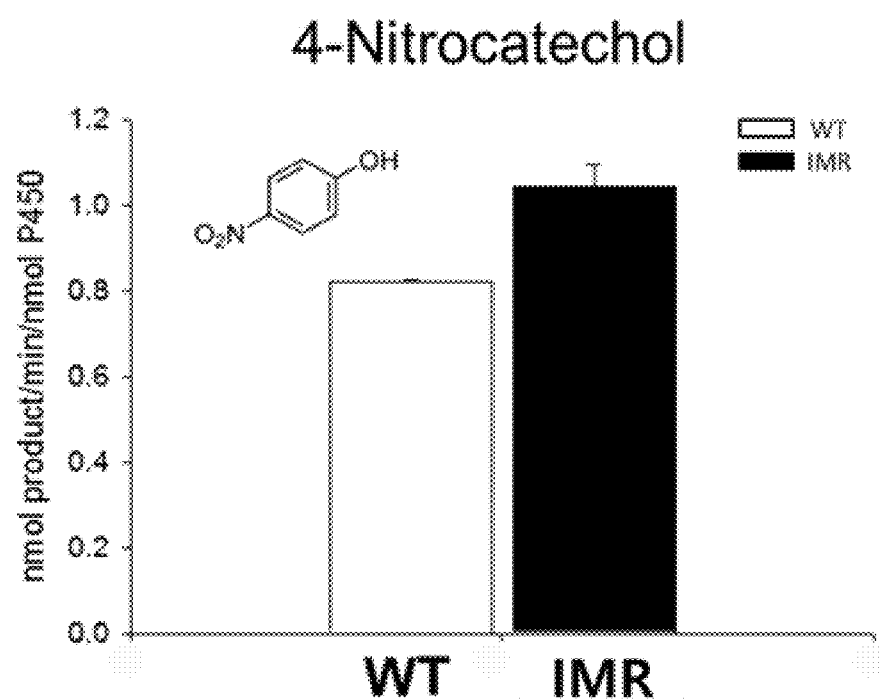
FIG. 9C is a graph illustrating results obtained by measuring and comparing enzyme reaction results in which each of two P450 proteins, i.e., the WT and IMR hydroxylates p-nitrophenol as a substrate to generate 4-nitrocatechol.

In order to confirm whether the increased enzyme activity of the cytochrome P450 BM3 IMR is equally exhibited in the substrates other than omeprazole, the enzyme activities for the substrates were compared and measured, and results thereof are illustrated in FIGS. 9A to 9C.

Specifically, when using the same substrate for cytochrome P450 BM3 WT and IMR, FIG. 9A illustrates the result obtained by hydroxylating 7-ethoxycoumarin to 7-OH coumarin, FIG. 9B illustrates the result obtained by hydroxylating 7-ethoxycoumarin to 3-OH 7-hydroxycoumarin, and FIG. 9C illustrates the result obtained by hydroxylating p-nitrophenol to 4-nitrocatechol.

As can be confirmed from the above results, in the case of the reconstituted cytochrome P450 BM3 IMR by the split intein after the independent expression of the oxygenase domain and reductase domain, the activity was increased from as little as about 30% to as much as about 80% with respect to the used substrates as compared to the wild type. This is a result different from the expectation that the WT and IMR will exhibit similar activity as a result of measuring the enzyme activities by correcting so that the purified cytochrome P450 BM3 wild type and IMR have the same amount of heme-containing protein, based on the spectrum results of the difference in CO. Recently, results have been reported that, when a codon encoding amino acid is substituted with a synonymous codon having a different codon usage, a change in a translation rate is induced, and the change in the translation rate results in a change in a folding pathway of the protein, and consequently may cause a difference in a tertiary structure of the protein. In addition, it is reported that the structural difference induced in this way affects the properties of the protein, for example, the antigen recognition ability of the antibody or the enzyme activity. While not intending to be limited by particular theories, from these results, it is deemed that independent expression of two domains causes a difference in the tertiary structure of the reconstituted cytochrome P450 BM3 IMR other than simple spatiotemporal separation expression, such that the difference in activity, such as seen in the above comparison results, appears. In addition, these results are consistent with the hypothesis that, like the expected effect of the present invention, protein splicing by the split intein will have a preference or have higher efficiency for reconstitution between domains having complete (well folded) structures.

From these results, it can be confirmed that the enzyme activity of the P450 protein produced by the recombinant expression vector system of the present invention is not improved depending on a specific substrate, but the activity of the enzyme itself is increased for various substrates, thereby resulting in prospective improvement in the enzymatic property. The effect of the present invention, which improves the activity without a metabolic engineering process or amino acid modification (inducing mutation) for enhancing the low heme content of the oxygenase domain that is a fundamental problem of the conventional cytochrome P450 protein, is a method which is clearly distinguished from directional artificial evolution techniques based upon a premise of improvement by changing the amino acid at the active site or other sites of the conventional P450 protein.

[Example 6] Comparison of Stability Between Bacterial Cytochrome P450 BM3 Wild Type and IMR When the structure of a protein is rigid or stable, less denaturation may occur due to degradation by the protease or unfolding of the structure. In the case of the reconstituted cytochrome P450 BM3 of the present invention, unlike a typical protein generated by artificial evolution technique in which an amino acid change, i.e., a structure change is presumed, it is unlikely that a large modification is caused in the protein tertiary structure. Therefore, rather than observing susceptibility for the proteases, the structural integrity of wild type and reconstituted cytochrome P450 BM3 was compared based on the denaturation degree during the long term storage. Since the denaturation of the protein structure directly affects the enzyme activity, the denaturation degree of the protein was evaluated by the activity of the enzyme remaining after storage for a period of time. To this end, the wild type and IMR purified for comparison of activity in Example 5 were stored for 5 days at 4° C., and the residual activity of the two proteins was measured. A method of measuring the activity of the two enzymes was as described in Example 5, and omeprazole was used as the substrate. The measurement results are illustrated in FIG. 10.

Figure 10:
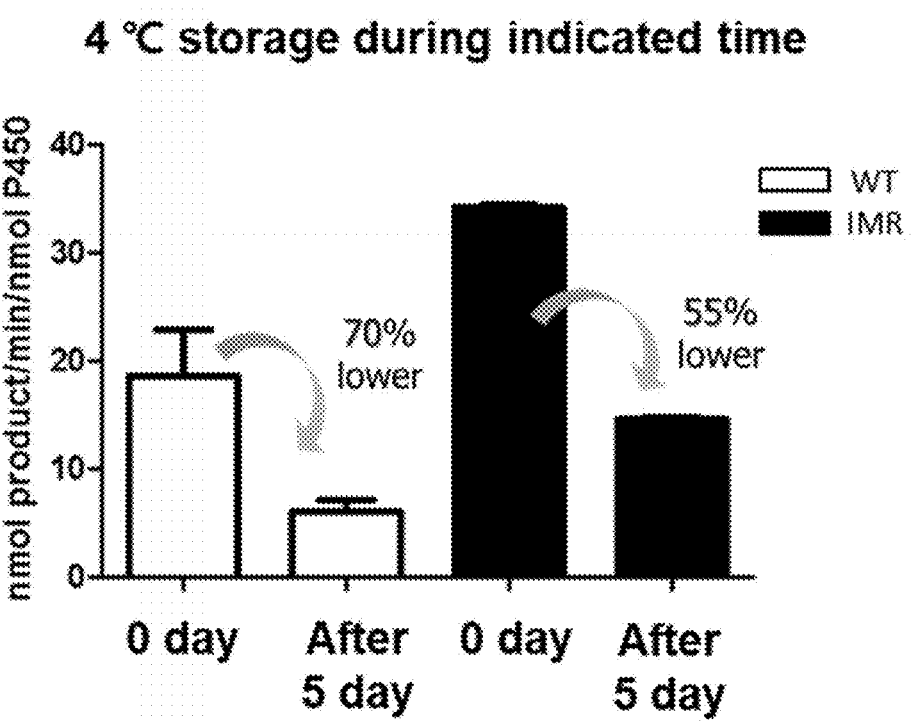
FIG. 10 is a graph illustrating results obtained by comparing stability in long-term storage of two purified P450 proteins, i.e., the WT and IMR.

As can be confirmed in FIG. 10, as a result of measuring the residual activity after storage under refrigeration for 5 days, the activity in the P450 BM3 wild type was reduced by 70% or more compared to before storage, but the activity in the IMR was reduced only by 55%. These results indirectly show that the reconstituted cytochrome P450 BM3 IMR has a more complete structure than the wild type.

[Example 7] Preparation of Hybrid Library Reconstituted by Domain Swapping of Bacterial Cytochrome P450 BM3 Oxygenase and Reductase As mentioned above, the bacterial cytochrome P450 BM3 is a protein having the oxygenase domain and the reductase domain, and is easy for industrial use due to a characteristic of being expressed in the cytoplasm rather than the cell membrane, and thus it is often used as a template for development of variants having specificity to various substrates through the directional artificial evolution technique. In addition, the bacterial cytochrome P450 BM3 is utilized as a template for development of an isozyme that can replace human-derived cytochrome P450, which is an important protein for toxicity evaluation but has a difficulty in expression and purification, such that researches on improvement of enzyme properties and a screening method thereof has been continuously conducted in various fields.

To improve the enzymatic properties of the bacterial P450 BM3, it is ideal that an optimal combination is created through simultaneous improvements of the oxygenase domain that oxidizes the substrate and the reductase domain that supplies the reducing power for activity. However, due to the long amino acid primary sequence forming the bacterial cytochrome P450 BM3 having a large molecular weight (119 kDa), it is very difficult to prepare a library capable of searching for all variants that can be produced by the protein artificial evolution technique. In many cases, mutation is induced only in the oxygenase domain that plays an important role in the enzyme activity and substrate specificity, or two domains are independently improved.

Figure 11:
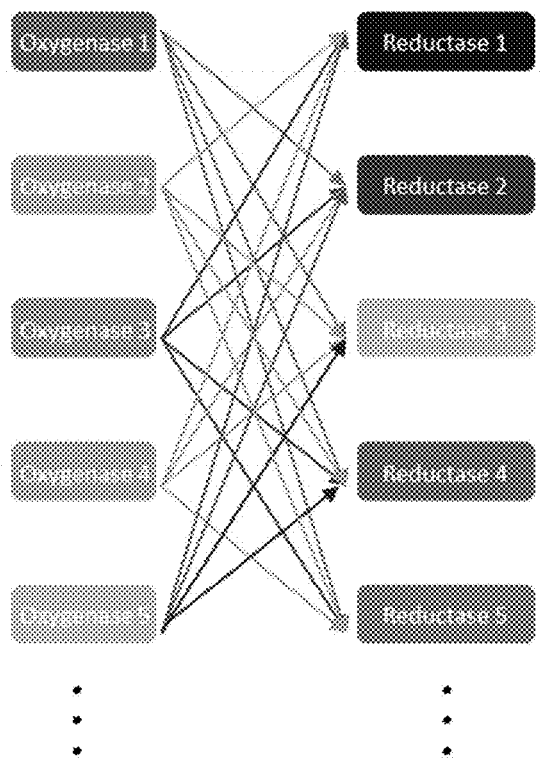
FIG. 11 is schematic diagrams illustrating a method of domain swapping of the oxygenase and reductase domains.
Figure 11:

In this situation, the independent expression and reconstitution method of the two domains of oxygenase and reductase developed in the present invention are techniques that can provide a different pathway from the protein artificial evolution technique which is a method of inducing amino acid mutation of a limited domain or region conventionally widely utilized in the art in order to improve protein properties. That is, it was expected that the inventive method would be used for improving enzyme properties by a method of combining cytochrome P450 BM3 oxygenase having excellent substrate specificity with reductase capable of delivering an optimal reducing power. Based on this expectation, after fusing and separating intein in which oxygenase domains and reductase domains of bacteria P450 BM3 R47L/F87V/L188Q, M11, 9-10A-87A, M1, 2C11, D6H10, 193-3 and 9C1 variants developed with isozymes of human cytochrome P450 CYP2E1, 2D6, 2C9, 2C19, 2D6, 3A4 and 1A2 are split, a hybrid library in which two domains are cross-substituted as simulated in FIG. 11 was prepared. Opposite ends of each domain of the variants are not differ from the sequence of the bacterial cytochrome P450 BM3, primers of SEQ ID NOs: 9 to 15 were used, and the hybrid library was prepared using the same method as in Example 1 and utilized to search for bacteria P450 BM3 hybrid variants having optimal activity. For the variant search, a 96 well plate-based chromogenic screening method, which is widely used in variant screening processes through the directional artificial evolution technique, was used. Although most of the used bacterial P450 BM3 variants have limitations in the preparation of various combinations of hybrid P450 BM3 because the mutation is concentrated in the oxygenase domain, it was confirmed that screening of variants having improved activity is possible through domain swapping of the reductase domain.

[Example 8] Preparation of Reconstituted Cytochrome P450 Hybrid Library Through Domain Swapping of Oxygenase and Reductase Domains Between Heterogeneous Cytochrome P450s In Example 7, the hybrid library in which the oxygenase domain and the reductase domain were cross-substituted with allogenic bacterial cytochrome P450 BM3 as a template was prepared, and it was confirmed that screening of variant having increased activity is possible.

Based on these results, the inventors have attempted to prepare a cross-substitution library consisting of heterogeneous cytochrome P450 and reductase domains, each domain deviating from one species of cytochrome P450, and having two domains independently. In this case, since the interaction of enzymes having different lengths and tertiary structural properties of amino acids can be searched, it was expected that it would be possible to screen variants that cannot be deduced from existing one template (bacteria P450 BM3).

Figure 12:
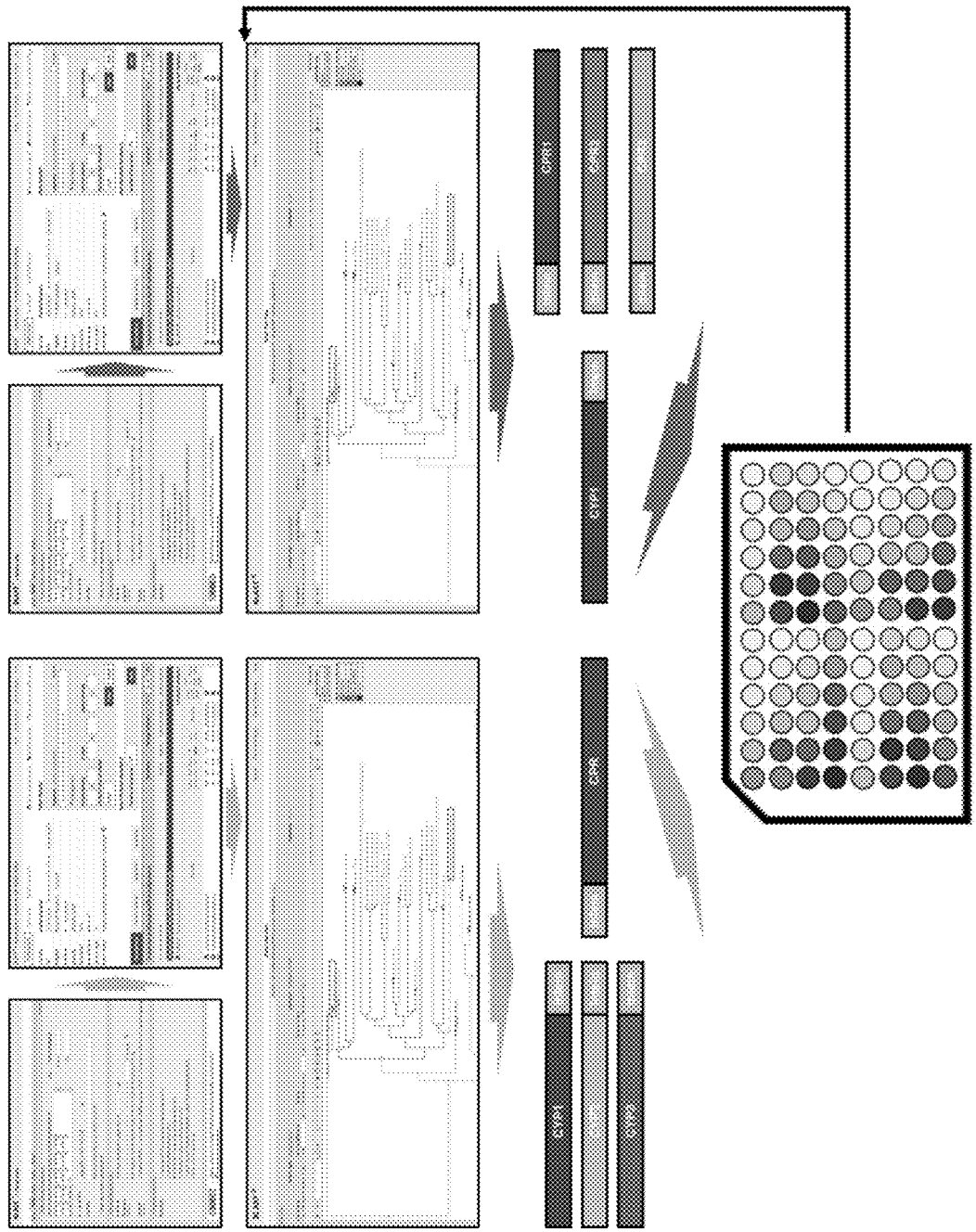
FIG. 12 is a schematic diagram illustrating a production process of hybrid cytochrome P450 consisting of heterologous oxygenase and reductase domains.

The hybrid library in which two domains are cross-substituted was sequentially subjected to a method of first fixing the reductase domain and substituting the oxygenase domain, and conversely, a method of fixing the oxygenase domain and substituting the reductase domain, thus to design the preparation of a cytochrome P450 hybrid library consisting of two domains derived from heterologous hosts (see FIG. 12).

The selection of each domain was performed in such a way that, based on the sequence of bacterial cytochrome P450 BM3 or human-derived cytochrome P450 with relatively well known enzymatic properties, a similar cytochrome P450 sequence was searched based on sequence homology of specific regions, i.e., conservative regions through PSI-BLAST search, and among the deduced proteins, sequences derived from microorganisms not belonging to *Bacillus*, plants or humans were extracted from proteins having 60 to 80% or more amino acid sequence homology. The extracted sequences were analyzed by using a phylogenetic tree to select upper sequences, then the lengths, conservation regions, and secondary structures of each domain of the bacterial P450 BM3 were compared, and then the entire regions, amino terminus region lengths, or carboxyl terminus region lengths were adjusted to fuse the intein split by the method used in Example 1. In this way, hybrid cytochrome P450 libraries having oxygenase domains derived from heterologous hosts and reductase domains of bacterial cytochrome P450 BM3 were prepared.

Subsequently, a hybrid cytochrome P450 having activity on the target substrate was searched for using the 96 well plate-based enzyme activity searching method to confirm the sequence analysis and origin of the screened oxygenase domain. Then, the amino acid sequences of the reductase domains of a species having the oxygenase domain were collected, then the reductase domain was searched for with the same method used for searching for the oxygenase domain. Subsequently, the split inteins were fused to produce a cytochrome P450 hybrid library derived from the heterogeneous hosts. As a result, it was confirmed that production of hybrid protein having various enzyme activities, stability, and different expression ratio (solubility), as well as increased heme content, is possible.

A sequence listing electronically submitted with the present application on Aug. 17, 2020 as an ASCII text file named 20200817_LC0142010_TU_SEQ, created on Aug. 17, 2020 and having a size of 40,000 bytes, is incorporated herein by reference in its entirety.

---

What is claimed is:

1. A recombinant vector for producing a cytochrome P450 oxygenase-reductase fusion protein in which cytochrome P450 oxygenase and reductase for the same are independently expressed and reconstituted, the recombinant vector comprising:
a first polynucleotide which encodes the cytochrome P450 oxygenase; a second polynucleotide which encodes the reductase; and a third polynucleotide which is interposed between the first and second polynucleotides and encodes a split intein.

2. The recombinant vector according to claim 1, wherein the first polynucleotide encodes a protein consisting of the amino acid sequence of SEQ ID NO: 1.

3. The recombinant vector according to claim 1, wherein the second polynucleotide encodes a protein consisting of the amino acid sequence of SEQ ID NO: 2.

4. The recombinant vector according to claim 1, wherein the third polynucleotide encodes a protein consisting of the amino acid sequence of SEQ ID NO: 6.

5. The recombinant vector according to claim 1, wherein the first polynucleotide consists of SEQ ID NO: 3, the second polynucleotide consists of SEQ ID NO: 4, and the third polynucleotide consists of SEQ ID NO: 5.

6. A host cell transformed with the recombinant vector according to claim 1.

7. The host cell according to claim 6, wherein the host cell is *Escherichia coli*.

8. A method for producing a reconstituted cytochrome P450 oxygenase-reductase fusion protein comprising: culturing the host cell according to claim 6.

9. A reconstituted cytochrome P450 oxygenase-reductase fusion protein having an increased heme content, enzyme activity or stability compared to a non-intein-mediated reconstituted cytochrome P450, which is produced by the method according to claim 8.

10. A composition for hydroxylation of a substrate comprising the reconstituted cytochrome P450 oxygenase-reductase fusion protein according to claim 9.

11. The composition according to claim 10, wherein the substrate is omeprazole, omeprazole sulfide, ethoxycoumarin or nitrophenol.

* * * * *